US012693251B2

(12) United States Patent
     Du

(10) Patent No.: US 12,693,251 B2
(45) Date of Patent: Jul. 28, 2026

(54) AUTOMATED OXYGEN-DEPENDENT BLOOD FUNCTION MEASUREMENT SYSTEMS AND METHODS

(71) Applicant: FLORIDA ATLANTIC UNIVERSITY BOARD OF TRUSTEES, Boca Raton, FL (US)

(72) Inventor: E Du, Boca Raton, FL (US)

(73) Assignee: FLORIDA ATLANTIC UNIVERSITY BOARD OF TRUSTEES, Boca Raton, FL (US)

( * ) Notice: Subject to any disclaimer, the term of this patent is extended or adjusted under 35 U.S.C. 154(b) by 179 days.

(21) Appl. No.: 18/675,920

(22) Filed: May 28, 2024

(65) Prior Publication Data

US 2025/0035576 A1 Jan. 30, 2025

Related U.S. Application Data

(60) Provisional application No. 63/516,269, filed on Jul. 28, 2023.

(51) Int. Cl.
| | |
|---|---|
| *G01N 27/08* | (2006.01) |
| *G01N 27/07* | (2006.01) |
| *G01N 33/49* | (2006.01) |
| *G01N 33/80* | (2006.01) |

(52) U.S. Cl.
CPC ............. *G01N 27/08* (2013.01); *G01N 27/07* (2013.01); *G01N 33/4915* (2013.01); *G01N 33/80* (2013.01)

(58) Field of Classification Search
CPC .... G01N 27/08; G01N 27/07; G01N 33/4915; G01N 33/80

USPC .......................................................... 324/693
See application file for complete search history.

(56) References Cited

U.S. PATENT DOCUMENTS

| | | | |
|---|---|---|---|
| 11,618,019 B2 | 4/2023 | Du et al. | |
| 12,158,458 B2 | 12/2024 | Du et al. | |
| 2010/0184115 A1* | 7/2010 | Lei ........................ | G01N 27/221 |
| | | | 703/2 |
| 2018/0202955 A1* | 7/2018 | Brun .................... | G01N 27/021 |
| 2018/0267021 A1 | 9/2018 | Suresh et al. | |
| 2020/0124567 A1* | 4/2020 | Gronowski ............ | G01N 27/49 |
| 2021/0164956 A1* | 6/2021 | Schweitzer ............ | G01N 27/06 |
| 2021/0219864 A1* | 7/2021 | Eom ...................... | A61B 5/681 |
| 2022/0228899 A1* | 7/2022 | Dalpez .................... | G01F 23/24 |

OTHER PUBLICATIONS

Chen, Yu-Shih, et al. "A review on microfluidics-based impedance biosensors." Biosensors 13.1 (2023): 83. (Year: 2023).*

(Continued)

*Primary Examiner* — Christopher P McAndrew
(74) *Attorney, Agent, or Firm* — Meunier Carlin & Curfman LLC

(57) ABSTRACT

Micro-electrical impedance-based assay systems (μZASs) for real-time monitoring of cellular response to an environmental condition are disclosed herein. An example microfluidic device can include: a cell channel configured to receive a sample substance (e.g., a blood sample), at least one gas channel operatively coupled to the cell channel defining a controlled testing environment of the microfluidic device, and a plurality of microfluidic impedance sensors configured to obtain electrical impedance-based measurements with respect to the sample substance.

18 Claims, 12 Drawing Sheets

(56) References Cited

OTHER PUBLICATIONS

Liu, Jia, et al. "Electrical impedance microflow cytometry with oxygen control for detection of sickle cells." Sensors and Actuators B: Chemical 255 (2018): 2392-2398. (Year: 2018).*

Akinsheye, et al., "Fetal Hemoglobin in Sickle Cell Anemia", Blood, vol. 118, pp. 19-27, Jul. 7, 2011.

Alapan, et al., "Emerging Point-of-Care Technologies for Sickle Cell Disease Screening and Monitoring", Expert Review of Medical Devices, vol. 13, No. 12, pp. 1073-1093, Nov. 22, 2016.

Alapan, et al., "Heterogeneous Red Blood Cell Adhesion and Deformability in Sickle Cell Disease", Scientific Reports, vol. 4, No. 7173, pp. 1-8, Nov. 24, 2014.

Barabino, et al., "Sickle Cell Biomechanics", Annual Review of Biomedical Engineering, vol. 12, pp. 345-367, Aug. 2010.

Beers, et al., "Imaging Flow Cytometry for Automated Detection of Hypoxia-induced Erythrocyte Shape Change in Sickle Cell Disease", American Journal of Hematology, vol. 89, No. 6, pp. 598-603, 2014.

Carmeliet, Peter, "Gene Targeting and Gene Transfer to Unravel the Molecular Basis of the Formation and Disorders of Blood Vessels", Verhandelingen—Koninklijke Academie Voor Geneeskunde van Belgie, vol. 62, pp. 31-68, Jan. 2000.

Cheung, et al., "Microfluidic Impedance-Based Flow Cytometry", Cytometry Part A, vol. 77A, No. 7, pp. 648-666, 2010.

Coelho, et al., "Sickle Cell Disease Severity Scoring: A Yet Unsolved Problem", European Journal of Haematology, vol. 8, No. 6, pp. 501-502, Dec. 2012.

Connes, et al., "Advances in Understanding the Pathogenesis of Cerebrovascular Vasculopathy in Sickle Cell Anaemia", British Journal of Haematology, vol. 161, No. 4, pp. 484-498, 2013.

Cucchi, et al., "Tetramethylbenzidine Staining Procedure after Starch Gel Electrophoresis of Human Haemoglobin", Comparative Haematology International, vol. 8, pp. 178-181, 1998.

Darrow, et al., "Visualizing Red Blood Cell Sickling and the Effects of Inhibition of Sphingosine Kinase 1 Using Soft X-Ray Tomography", Journal of Cell Science, vol. 129, No. 18, pp. 3511-3517, 2016.

Das, et al., "Electrical Characterization of Suspended Hela Cells Using ECIS Based Biosensor", 2012 Sixth International Conference on Sensing Technology (ICST), pp. 734-737, 2012.

Dieujuste, et al., "A Portable Impedance Microflow Cytometer for Measuring Cellular Response to Hypoxia", Biotechnology and Bioengineering, vol. 118, pp. 4041-4051, 2021.

Dona, et al., "An Impedimetric Assay for the Identification of Abnormal Mitochondrial Dynamics in Living Cells", Electrophoresis, vol. 42, pp. 163-170, 2021.

Du, et al., "Electric Impedance Microflow Cytometry for Characterization of Cell Disease States", Lab Chip, vol. 13, pp. 3903-3909, 2013.

Du, et al., "Electrohydrodynamic-Mediated Dielectrophoretic Separation and Transport Based on Asymmetric Electrode Pairs", Electrophoresis, vol. 29, pp. 5017-5025, 2008.

Du, et al., "Erythrocyte Membrane Failure by Electromechanical Stress", Applied Sciences, vol. 8, No. 174, pp. 1-10, Jan. 25, 2018.

Du, et al., "Faster Sickling Kinetics and Sickle Cell Shape Evolution during Repeated Deoxygenation and Oxygenation Cycles", Experimental Mechanics, vol. 59, pp. 319-325, 2019.

Du, et al., "Kinetics of Sickle Cell Biorheology and Implications for Painful Vasoocclusive Crisis", Proceedings of the National Academy of Sciences of the United States of America, vol. 112, No. 5, pp. 1422-1427, Feb. 3, 2015.

Du, et al., "Microfluidic Pumping Optimization in Microgrooved Channels With Ac Electrothermal Actuations", Applied Physics Letters, vol. 96, No. 3, pp. 034102-1-034102-3, 2010.

Du, et al., "Quantification of Anti-Sickling Effect of Aes-103 in Sickle Cell Disease Using an in Vitro Microfluidic Assay", Blood, vol. 124, No. 21, 3 pages, Dec. 6, 2014.

Du, et al., "Quantitative Biomechanics of Healthy and Diseased Human Red Blood Cells Using Dielectrophoresis in a Microfluidic System", Extreme Mechanics Letters, vol. 1, pp. 35-41, Dec. 2014.

Eaton, et al., "Editorial Hypothesis: Delay Time of Gelation: A Possible Determinant of Clinical Severity in Sickle Cell Disease", Blood, vol. 47, No. 4, pp. 621-627, Apr. 1976.

Eaton, et al., "Hemoglobin S Gelation and Sickle Cell Disease", Blood, vol. 70, No. 5, pp. 1245-1266, 1987.

Ederveen, Joke C., "A Practical Approach to Biological Assay Validation", Dutch Ministry of Housing, Spatial Planning and the Environment (VROM), Hoofdorp, 106 pages, 2010.

Embury, Stephen H., "The Not-So-Simple Process of Sickle Cell Vasoocclusion", Microcirculation, vol. 11, pp. 101-113, 2004.

Frenette, et al., "Sickle Cell Vaso-Occlusion: Multistep and Multicellular Paradigm", Current Opinion in Hematology, vol. 9, No. 2, pp. 101-106, Mar. 2002.

Guruprasad, et al., "Integrated Automated Particle Tracking Microfluidic Enables High-throughput Cell Deformability Cytometry for Red Cell Disorders", American Journal of Hematology, vol. 94, pp. 189-199, 2019.

Herisson, et al., "Posterior Reversible Encephalopathy Syndrome in Stroke-prone Spontaneously Hypertensive Rats on High-salt Diet", Journal of Cerebral Blood Flow & Metabolism, vol. 39, No. 7, pp. 1232-1246, 2019.

Higgin, et al., "Sickle Cell Vasoocclusion and Rescue in a Microfluidic Device", Proceedings of the National Academy of Sciences of the United States of America, vol. 104, No. 51, pp. 20496 -20500, Dec. 18, 2007.

Holmes, et al., "Leukocyte Analysis and Differentiation using High Speed Microfluidic Single Cell Impedance Cytometry", Lab on a Chip, vol. 9, No. 20, pp. 2881-2889, 2009.

Horiuchi, et al., "Estimation of Fetal Hemoglobin Levels in Individual Red Cells via Fluorescence Image Cytometry", Cytometry, vol. 20, pp. 261-267, 1995.

Hosseini, et al., "Cellular Normoxic Biophysical Markers of Hydroxyurea Treatment in Sickle Cell Disease", Proceedings of the National Academy of Sciences of the United States of America, vol. 113, No. 34, pp. 9527-9532, Aug. 23, 2016.

Ilyas, et al., "Smartphone-Based Sickle Cell Disease Detection and Monitoring for Point-of-Care Settings", Biosensors and Bioelectronics, vol. 165, 112417 page, Oct. 1, 2020.

Kaul, et al., "Microvascular Sites and Characteristics of Sickle Cell Adhesion to Vascular Endothelium in Shear Flow Conditions: Pathophysiological Implications", Proceedings of the National Academy of Sciences of the United States of America, vol. 86, pp. 3356-3360, Jan. 5, 1989.

Knowlton, et al., "Sickle Cell Detection Using a Smartphone", Scientific Reports, vol. 5, No. 15022, pp. 1-11, Oct. 22, 2015.

Kobayashi, et al., "Effects of L-Carnitine and Palmitoylcarnitine on Membrane Fluidity of Human Erythrocytes", Biochimica et Biophysica Acta (BBA)—Biomembranes, vol. 986, pp. 83-88, Nov. 17, 1989.

Labie, et al., "Common Haplotype Dependency of High G Gamma-Globin Gene Expression and High Hb F Levels in Beta-thalassemia and Sickle Cell Anemia Patients", Proceedings of the National Academy of Sciences of the United States of America, vol. 82, pp. 2111-2114, Apr. 1985.

Li, et al., "Patient-Specific Blood Rheology in Sickle-Cell Anaemia", Interface Focus, vol. 6, pp. 1-9, 2016.

Li, et al., "Patient-Specific Modeling of Individual Sickle Cell Behavior Under Transient Hypoxia", PLOS Computational Biology, vol. 13, No. 3, pp. 1-17, Mar. 13, 2017.

Liu, et al., "Biosensors for Detection of Human Placental Pathologies: A Review of Emerging Technologies and Current Trends", Translational Research, vol. 213, pp. 23-49, Nov. 2019.

Liu, et al., "Dielectric Spectroscopy of Red Blood Cells in Sickle Cell Disease", Electrophoresis, vol. 42, pp. 667-675, 2021.

Liu, et al., "Electrical Equivalent Circuit Model of Sickle Cell", ASME 2017 International Mechanical Engineering Congress and Exposition, 5 pages, Jan. 10, 2018.

Liu, et al., "Electrical Impedance Characterization of Erythrocyte Response to Cyclic Hypoxia in Sickle Cell Disease", ACS Sensors Journal, vol. 4, pp. 1783-1790, May 14, 2019.

Liu, et al., "Electrical Impedance Microflow Cytometry With Oxygen Control for Detection of Sickle Cells", Sensors and Actuators B: Chemical, vol. 255, pp. 2392-2398, Feb. 2018.

(56) References Cited

OTHER PUBLICATIONS

Losek, et al., "Diagnostic Value of Anemia, Red Blood Cell Morphology, and Reticulocyte Count for Sickle Cell Disease", Annals of Emergency Medicine, vol. 21, No. 8, pp. 915-918, Aug. 1992.

Lu, et al., "Deoxygenation Reduces Sickle Cell Blood Flow at Arterial Oxygen Tension", Biophysical Journal, vol. 110, No. 12, pp. 2751-2758, Jun. 21, 2016.

Lu, et al., "Oxygen-Dependent Flow of Sickle Trait Blood as an in Vitro Therapeutic Benchmark for Sickle Cell Disease Treatments", American Journal of Hematology, vol. 93, pp. 1227-1235, 2018.

Ma, et al., "Fetal Hemoglobin in Sickle Cell Anemia: Genetic Determinants of Response to Hydroxyurea", The Pharmacogenomics Journal, vol. 7, pp. 386-394, 2007.

Man, et al., "Leukocyte Adhesion to P-Selectin and the Inhibitory Role of Crizanlizumab in Sickle Cell Disease: A Standardized Microfluidic Assessment", Blood Cells, Molecules, and Diseases, vol. 83, 102424 page, Jul. 2020.

Manwani, et al., "Vaso-Occlusion in Sickle Cell Disease: Pathophysiology and Novel Targeted Therapies", Blood, vol. 122, No. 24, pp. 3892-3898, Dec. 5, 2013.

Modell, et al., "Global Epidemiology of Haemoglobin Disorders and Derived Service Indicators", Bulletin of the World Health Organization, vol. 86, No. 6, pp. 480-487, Jun. 2008.

Moreno, et al., "CRISPR/Cas9-Modified Hematopoietic Stem Cells-present and Future Perspectives for Stem Cell Transplantation", Bone Marrow Transplantation, vol. 54, pp. 1940-1950, 2019.

Mozzarelli, et al., "Delay Time of Hemoglobin S Polymerization Prevents Most Cells from Sickling in Vivo", Science, vol. 237, No. 4814, pp. 500-506, Jul. 31, 1987.

Muenster, et al., "Exposure of Stored Packed Erythrocytes to Nitric Oxide Prevents Transfusion-associated Pulmonary Hypertension", Anesthesiology, vol. 125, No. 5, pp. 952-963, Nov. 2016.

Nebor, et al., "Frequency of Pain Crises in Sickle Cell Anemia and Its Relationship with the Sympatho-Vagal Balance, Blood Viscosity and Inflammation", Haematologica, vol. 96, No. 11, pp. 1589-1594, 2011.

Ninno, et al., "High-Throughput Label-free Characterization of Viable, Necrotic and Apoptotic Human Lymphoma Cells in a Coplanar-electrode Microfluidic Impedance Chip", Biosensors and Bioelectronics, vol. 150, 111887 page, Feb. 15, 2020.

Noguchi, et al., "Intracellular Polymerization of Sickle Hemoglobin. Effects of Cell Heterogeneity", The Journal of Clinical Investigation, vol. 72, No. 3, pp. 846-852, Sep. 1983.

Odievre, et al., "Pathophysiological Insights in Sickle Cell Disease", The Indian Journal of Medical Research, vol. 134, No. 4, pp. 532-537, Oct. 2011.

Orkin, et al., "Emerging Genetic Therapy for Sickle Cell Disease", Annual Review of Medicine, vol. 70, pp. 257-271, 2019.

Oyenike, et al., "In-Vitro Anti-Sickling and Membrane Stability Potentials of Mishenland Polyherbal Extract on Sickle Red Blood Cells", The Egyptian Journal of Haematology, vol. 44, pp. 65-71, 2019.

Parrow, et al., "Measuring Deformability and Red Cell Heterogeneity in Blood by Ektacytometry", Journal of Visualized Experiments (JoVE), vol. 131, pp. 1-9, Jan. 2018.

Pethig, et al., "The Passive Electrical Properties of Biological Systems: Their Significance in Physiology, Biophysics and Biotechnology", Physics in Medicine & Biology, vol. 32, No. 8, pp. 933-970, 1987.

Platt, Orahs. , "Hydroxyurea for the Treatment of Sickle Cell Anemia", The New England Journal of Medicine, vol. 358, pp. 1362-1369, Mar. 27, 2008.

Poillon, et al., "Intracellular Hemoglobin S Polymerization and the Clinical Severity of Sickle Cell Anemia", Blood, vol. 91, No. 5, pp. 1777-1783, Mar. 1, 1998.

Qiang, "Continuous Cell Sorting by Dielectrophoresis in a Straight Microfluidic Channel", ASME 2018 International Mechanical Engineering Congress and Exposition, 5 pages, Jan. 15, 2019.

Qiang, et al., "Dynamic Fatigue Measurement of Human Erythrocytes Using Dielectrophoresis", Acta Biomaterialia, vol. 57, pp. 352-362, Jul. 15, 2017.

Qiang, et al., "Electrical Impedance Detection of Sickle Cell Vaso-Occlusion in Microfluidic Capillary Structures", bioRxiv, 6 pages, 2020.

Qiang, et al., "Experimental Electromechanics of Red Blood Cells Using Dielectrophoresis-Based Microfluidics", Systems and Materials, vol. 6, pp. 129-134, 2019.

Qiang, et al., "In Vitro Assay for Single-Cell Characterization of Impaired Deformability in Red Blood Cells Under Recurrent Episodes of Hypoxia", Lab on a Chip, vol. 21, pp. 3458-3470, 2021.

Qiang, et al., "Mechanical Fatigue of Human Red Blood Cells", Proceedings of the National Academy of Sciences of the United States of America, vol. 116, No. 40, pp. 19828-19834, Oct. 1, 2019.

Qiang, et al., "Modeling Erythrocyte Electrodeformation in Response to Amplitude Modulated Electric Waveforms", Scientific Reports, vol. 8, No. 10224, pp. 1-10, Jul. 5, 2018.

Sarode, et al., "Blood Bank Issues Associated with Red Cell Exchanges in Sickle Cell Disease", Journal of Clinical Apheresis, vol. 21, pp. 271-273, 2006.

Stamatoyannopoulos, et al., "A New Form of Hereditary Persistence of Fetal Hemoglobin in Blacks and Its Association With Sickle Cell Trait", Blood, vol. 46, No. 5, pp. 683-692, Nov. 1975.

Steinberg, Martin H., "Sickle Cell Anemia, the First Molecular Disease: Overview of Molecular Etiology, Pathophysiology, and Therapeutic Approaches", The Scientific World Journal, vol. 8, pp. 1295-1324, Dec. 25, 2008.

Swerdlow, et al., "Red Cell Exchange in Sickle Cell Disease", American Society of Hematology, vol. 1, pp. 48-53, 2006.

Switzer, et al., "Pathophysiology and Treatment of Stroke in Sickle-Cell Disease: Present and Future", The Lancet Neurology, vol. 5, No. 6, pp. 501-512, Jun. 2006.

Tian, et al., "Rapid Characterization of Water Diffusion in Polymer Specimens Using a Droplet-Based Method", Langmuir, vol. 36, No. 26, pp. 7309-7314, 2020.

Usami, et al., "Effect of Deoxygenation on Blood Rheology in Sickle Cell Disease", Microvascular Research, vol. 9, No. 3, pp. 324-334, May 1975.

Valdez, et al., "A Microfluidic Platform for Simultaneous Quantification of Oxygen-dependent Viscosity and Shear Thinning in Sickle Cell Blood", APL Bioengineering, vol. 3, No. 4, 10 pages, Nov. 15, 2019.

Vekilov, Peter G., "Sickle-Cell Haemoglobin Polymerization: Is It the Primary Pathogenic Event of Sickle-cell Anaemia?", British Journal of Haematology, vol. 139, pp. 173-184, 2007.

Vichinsky, et al., "A Phase 3 Randomized Trial of Voxelotor in Sickle Cell Disease", The New England Journal of Medicine, vol. 381, No. 6, pp. 509-519, Aug. 8, 2019.

Weatherall, David J., "The Inherited Diseases of Hemoglobin are an Emerging Global Health Burden", Blood, vol. 115, No. 22, pp. 4331-4336, Jun. 3, 2010.

* cited by examiner

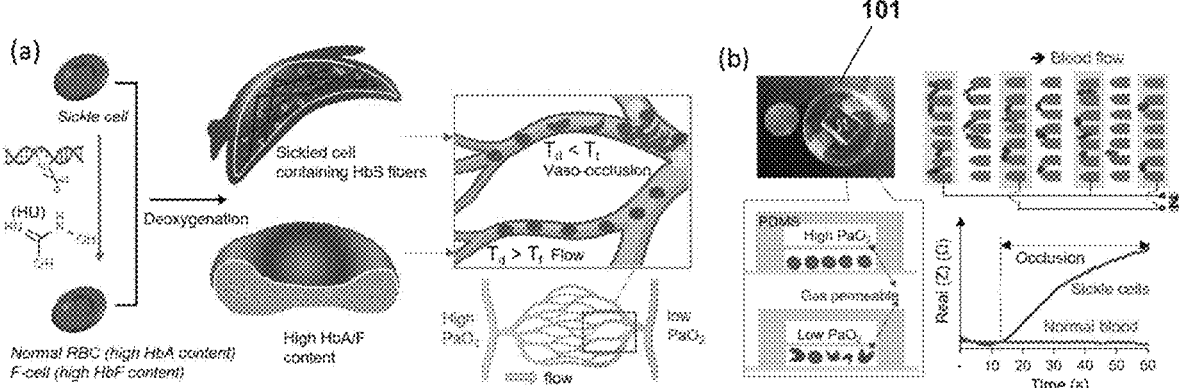
FIG. 1A                    FIG. 1B (A)
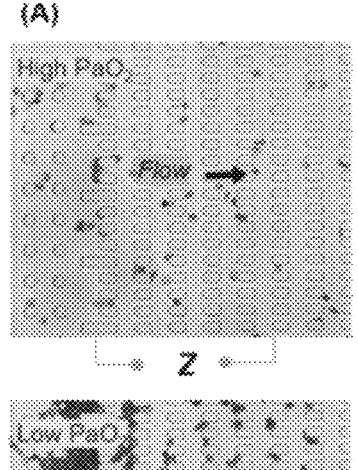
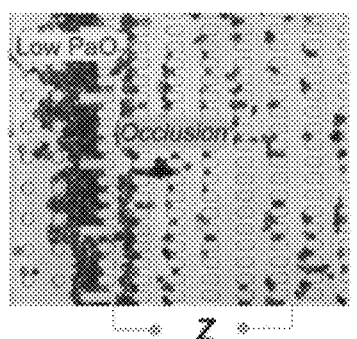
FIG. 8A
(B)
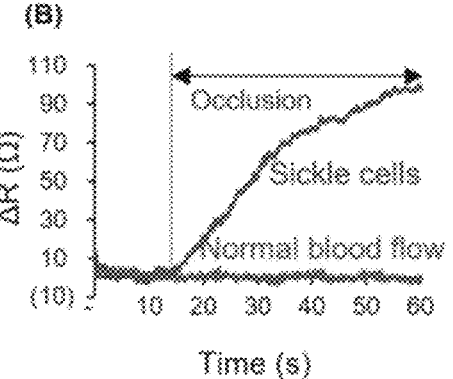
Time (s)
FIG. 8B
(C)
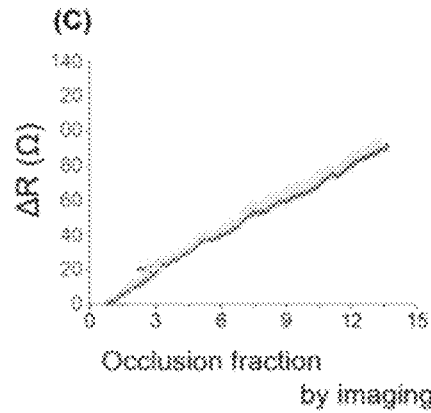
Occlusion fraction
by imaging
FIG. 8C

912

Impedance reading device

910

Push-fit module (B)

901

Microfluidic chip

Pogo pins    903b

903a

907b

Lid

907a

Electrodes contact pads (A)

(A)

1002a

Detection
well

1002b

Detection
micro-slits (B)     1004

$\Delta P = \rho g \Delta h$ $\Theta = [0,15°]$

1010

(A) Sickling assay

(B) Rheology assay t (s) FIG. 12A t (s) FIG. 12B

| (C) | Parameter | @ 65 mm Hg | @ 20 mm Hg |
|---|---|---|---|
| Sickling index, Š | fraction | $\Delta R_{65}$ | $\Delta R_{20}$ |
| | rate | $\int_0^{t1} (\Delta R - \Delta R_{t1}) dt / \Delta R_{65}$ | $\int_{t1}^{t2} (\Delta R - \Delta R_{t2}) dt / \Delta R_{20}$ |
| Rheology index, Ř | fraction | $\Delta R^*_{65}$ | $\Delta R^*_{20}$ |
| | rate | $\int_0^{t1} \Delta R^* dt / \Delta R^*_{65}$ | $\int_{t1}^{t2} \Delta R^* dt / \Delta R^*_{20}$ |

AUTOMATED OXYGEN-DEPENDENT BLOOD FUNCTION MEASUREMENT SYSTEMS AND METHODS

CROSS-REFERENCE TO RELATED APPLICATIONS

This application claims priority to and the benefit of U.S. Provisional Application No. 63/516,269, titled "AUTO-MATED OXYGEN-DEPENDENT BLOOD FUNCTION MEASUREMENT SYSTEMS AND METHODS," filed on Jul. 28, 2023, the content of which is hereby incorporated by reference in its entirety.

STATEMENT REGARDING FEDERALLY SPONSORED RESEARCH OR DEVELOPMENT

This invention was made with government support under grant number 2032730 and 1941655 awarded by the National Science Foundation. The government has certain rights in the invention.

BACKGROUND

Existing microfluidic assays of sickle cell functions (e.g., cell sickling, adhesion, deformability, occlusion, and viscosity) rely heavily on sophisticated infrastructure to support testing (e.g., microscope, pumps, image data storage) and intricate computer algorithms to process/analyze microscopic images/videos. Therefore, these barriers together with the cumbersome procedures involved in microfluidic operations (e.g., loading samples and driving the flow using tubing, needles, syringes) have prevented these novel microfluidic assays from wide clinical adoption.

There is a need for improved systems and methods for testing and monitoring cell behaviour associated with various conditions such as Sickle Cell Disease (SCD).

SUMMARY

Embodiments of the present disclosure provide electrical impedance-based systems and devices for real-time measurement of cell rheology (e.g., deformability and microvascular occlusion) in microfluidic mimics of capillary structures.

Embodiments of the present disclosure provide portable, standalone, micro-electrical impedance-based assay systems ($\mu$ZAS) for rapid (<10 min) measurement of $O_2$-dependent sickle cell functional properties from ultrasmall volumes (1-10 $\mu$L, or higher) of whole blood. In some implementations, the $\mu$ZAS comprises a pre-programmed instrument and one or more (e.g., two) microfluidic chips (disposable) for measurement of: (i) cell sickling events (e.g., rate of cell sickling, and fraction of sickled cells induced by intracellular HbS polymerization), and (ii) sickle cell rheology (deformability and obstruction in micro-slits). The exemplary instrument can comprise multiple modules, including (i) a snap fit module with or without magnetic force enabled (to achieve quick electrical connection of microfluidic chips to the instrument), (ii) gas valve(s) and gas cartridges (to define the $O_2$ environment of testing), (ii) a gravity-driven flow module, and (iv) a monitor.

Existing microfluidic designs, especially those with electrical-fluidic-gas coupling, require users to manually operate and interact with the control/testing system at specific time-points. This largely lowers the usability of the microfluidics, especially by those who do not have sufficient training or engineering skills. Embodiments of the present disclosure provide an easy-to-use, fully automated blood-to-results assay that can be adopted widely for clinical practice and operated by non-engineers. In some embodiments, the main instrument can be designed as a simple push-button-to-start measuring system. The program embedded in the instrument will perform the microfluidic testing and report the results from the specific assay without further user interaction, after the blood is loaded into the microfluidic device and gas supply tubing inserted.

In some implementations, a micro-electrical impedance-based assay system ($\mu$ZAS) for real-time monitoring of cellular response to an environmental condition (e.g., $PaO_2$ transition) is provided. The system can include at least one microfluidic device comprising: a cell channel configured to receive a sample substance (e.g., blood); at least one gas channel operatively coupled to the cell channel defining a controlled testing environment of the microfluidic device (e.g., operatively coupled to at least one supply of a testing gaseous substance, such as oxygen); and a plurality of microfluidic impedance sensors (e.g., a multi-well microfluidic impedance sensor array or z-plate) configured to obtain electrical impedance-based measurements with respect to the sample substance, wherein the at least one microfluidic device is operatively coupled to a gravity driven flow module configured to generate a gravity-driven hydrostatic pressure difference to drive a flow of the sample substance through the at least one microfluidic device; and a measurement instrument (e.g., simple push-button-to-start) operatively coupled to the at least one microfluidic device that is configured to control the testing environment (e.g., control 3-way $PaO_2$ valve) of the at least one microfluidic device.

In some implementations, the $\mu$ZAS further includes: a controller operatively coupled to the measurement instrument that is configured to determine and output at least one measurement value in relation to the sample substance to provide quantitative assessment of a hematological condition or outcome.

In some implementations, the controller is configured to determine at least one of a sickling index and/or sickle cell rheology.

In some implementations, the controller is configured to detect a change in electrical impedance above a predetermined threshold that is indicative of an abnormal blood flow.

In some implementations, the controller is configured to detect a $PaO_2$ transition resulting from resistance to electric currents associated with a corresponding sickling event.

In some implementations, the $\mu$ZAS further includes: a display device or monitor operatively coupled to the $\mu$ZAS and the controller configured to output at least a portion of the electrical impedance-based measurement values.

In some implementations, at least one of the electrical impedance-based measurement values is used to evaluate treatment efficacy for sickle cell disease, determine a biophysical marker of diabetes, assess whether blood flow is normal under hypoxia, or to evaluate dosage-dependencies of blood flow on medications.

In some implementations, the measurement instrument is configured to measure a rate of blood flow through the at least one microfluidic device.

In some implementations, the at least one microfluidic device and the measurement instrument are operatively coupled to one another via a magnetic, force, or snap-fit connection.

In some implementations, the at least one microfluidic device further includes at least one microstructure for measuring a flow condition or obstruction.

In some implementations, the at least one gas channel includes or defines a gas channel network.

In some implementations, the at least one gas channel is configured to supply at least a first gaseous substance and a second gaseous substance.

In some implementations, the gas channel network includes at least one valve and at least one gas cartridge defining the controlled testing environment.

In some implementations, the gas channel network includes a single inlet and a single outlet.

In some implementations, the plurality of microfluidic impedance sensors is positioned within the gas channel network.

In some implementations, the gravity driven flow module includes a rocker module configured to facilitate programmable gravity-driven flow.

In some implementations, the $\mu$ZAS is configured for blood testing under a plurality of controlled $O_2$ conditions or $PaO_2$ conditions.

In some implementations, the at least one microfluidic device includes at least one disposable chip.

In some implementations, the plurality of microfluidic impedance sensors includes 16 microfluidic impedance sensors.

In some implementations, a micro-electrical impedance-based assay system ($\mu$ZAS) for real-time monitoring of cellular response to an environmental condition that includes a plurality of microfluidic devices is provided. In some examples, each microfluidic device includes: a cell channel configured to receive a sample substance; at least one gas channel operatively coupled to the cell channel defining a controlled testing environment of each of the plurality of microfluidic devices; and a plurality of microfluidic impedance sensors configured to obtain electrical impedance-based measurements with respect to the sample substance, wherein: each microfluidic device is operatively coupled to gravity driven flow module (e.g., rocker module) configured to generate a gravity-driven hydrostatic pressure difference to drive a flow of the sample substance through each respective microfluidic device, and the plurality of microfluidic devices is operatively coupled to a measurement instrument that is configured to control a testing environment of each microfluidic device.

Additional advantages of the disclosed systems and methods will be set forth in part in the description that follows and, in part, will be obvious from the description. The advantages of the disclosed systems and methods will be realized and attained by means of the elements and combinations particularly pointed out in the appended claims. It is to be understood that both the foregoing general description and the following detailed description are exemplary and explanatory only and are not restrictive of the disclosed systems and methods, as claimed.

BRIEF DESCRIPTION OF THE DRAWINGS

The accompanying drawings, which are incorporated in and constitute a part of this specification, illustrate embodiments and, together with the description, serve to explain the principles of the methods and systems.

FIG. 1A is a schematic diagram depicting HbS polymerization which is the fundamental mechanism of Sickle Cell Disease (SCD) pathophysiology.

FIG. 1B shows an example microfluidic impedance sensor that provides sickle cell rheological measurement under controlled $PaO_2$ and in real-time.

FIG. 8A illustrates steady flow of sickle cells under high $PaO_2$ and obstruction at micro-slits by rigid, sickled cells under fully deoxygenated condition.

FIG. 8B is a graph showing real time impedance (real part, R) monitoring of cell rheology along when $PaO_2$ decreases to 0 mm Hg.

FIG. 8C is a graph demonstrating strong linearity in sickle cell occlusion (time-dependent measurement) between impedance signal and microscopic analysis.

FIG. 11A shows a three-dimensional (3D) model of an example instrument in accordance with certain embodiments described herein.

FIG. 11B shows a diagram of the microcontroller-relay system with single push button to start in accordance with certain embodiments described herein.

FIGS. 11A-11D are diagrams illustrating a pre-programmed instrument for automated blood-to results assays of $O_2$-dependent sickle cell functions in accordance with certain embodiments described herein.

FIG. 12A illustrates a Sickling assay.

FIG. 12B illustrates a Rheology assay.

Figures 2A, 2B, 2C:
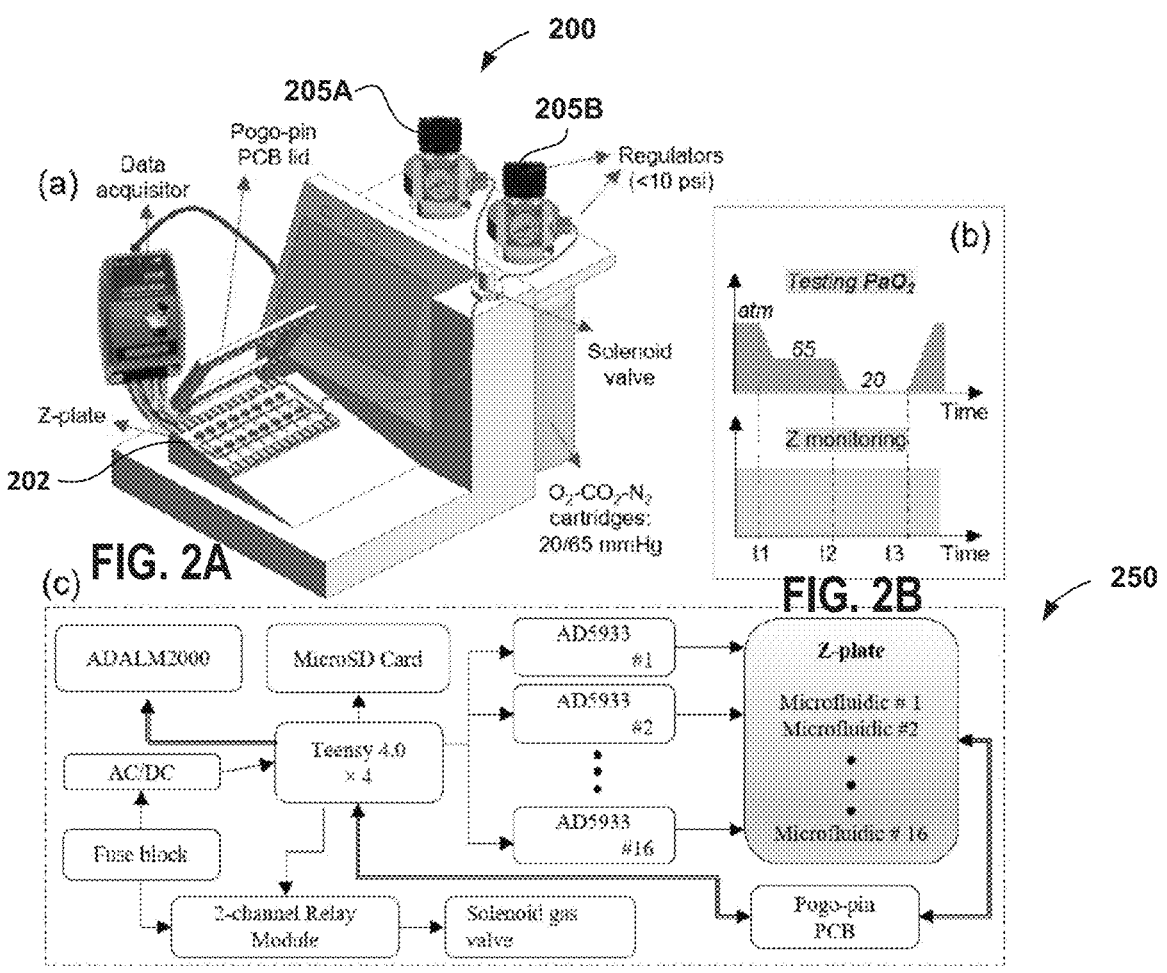
FIG. 2A is a schematic diagram depicting an example micro-electrical impedance-based assay system in accordance with certain embodiments described herein.
FIG. 2B illustrates program $PaO_2$ control and impedance monitoring in accordance with certain embodiments described herein.
FIG. 2C is a diagram of a microcontroller-relay system for impedance monitoring in accordance with certain embodiments described herein.

It should be appreciated that the logical operations described herein with respect to the various figures may be implemented (1) as a sequence of computer-implemented acts or program modules (i.e., software) running on a computing device (e.g., the computing device described in FIG. 13), (2) as interconnected machine logic circuits or circuit modules (i.e., hardware) within the computing device and/or (3) a combination of software and hardware of the computing device.

DETAILED DESCRIPTION

Each and every feature described herein, and each and every combination of two or more of such features, is included within the scope of the present disclosure, provided that the features included in such a combination are not mutually inconsistent.

Development of the µZAS is based on our microfluidic innovations that can rapidly quantify sickle cell functional properties under controlled $PaO_2$ (partial pressure of oxygen), as well as electrical impedance sensing innovations. Examples of these systems and devices are described in more detail in U.S. patent application Ser. No. 16/585,897, filed on Sep. 27, 2019, and entitled "PORTABLE ELECTRICAL IMPEDANCE-BASED BLOOD TESTING DEVICE FOR DIAGNOSIS AND MONITORING SICKLE CELL DISEASE," and U.S. patent application Ser. No. 17/313,235, filed on May 6, 2021, and entitled "VASCULAR OCCLUSION TESTING DEVICE", the contents of which are incorporated herein by reference in their entirety.

Embodiments of the present disclosure convert optical signals of sickle cell characteristics into electrical signals for real-time, sensitive, and automated analyses. Described herein are systems and apparatuses that improve portability and usability of microfluidic devices that can be fully automated. Operation of the example µZAS is compatible with standard micropipette operation and does not require any external pumping action, microbore tubing connection, or wire soldering.

Analysis of sickle cell functional properties in microfluidic devices requires recording and processing microscopic video, which cannot be easily implemented for automated blood-to-results testing. Embodiments of the present disclosure use electrical impedance as an alternative method to optical microscopy.

Sickle cell disease: remarkable cellular and clinical heterogeneities. Sickle cell disease (SCD) is a genetically inherited hemoglobin disorder [3-5], caused by a point mutation in the beta-globin gene, resulting in sickle hemoglobin (HbS) [6]. At low levels of partial pressure of oxygen ($PaO_2$), HbS polymerizes inside red blood cells (RBCs) and results in sickle shaped cells [7,8]. Polymerization of deoxygenated HbS is the fundamental pathophysiological mechanism of the SCD9 (FIG. 1A), contributing to vaso-occlusion, the hallmark of SCD, and the primary mechanism underlying pain, tissue damage, bone necrosis and infarcts, infections, acute chest syndrome, stroke and even death [10,11]. SCD exhibits extreme clinical heterogeneity [12,13]. Painful crises vary significantly in terms of frequency and pain scale and remains unpredictable with no clear precipitating factors [15]. The degree of cell sickling events are strongly dependent on the intracellular HbS concentration and water content [16,17]. Sickle cell morphology and rheology vary remarkably among SCD patients, depending on genotype and therapeutic intervention [13,18-21].

Sickle cell functional properties are new biophysical markers of SCD heterogeneity and severity. Abnormalities in sickle cell functions ($O_2$-dependent alternations in morphology and rheology) have been demonstrated to be significant physiological markers of sickle cell disease severity and patient-specific response to HbS targeting therapies [23]. Sickle cells exhibit abnormal morphology and rheology (reduced deformability), as compared to normal RBCs. Under low $PaO_2$, HbS polymerization leads to cell sickling events (alterations in cell morphology) [24,25] and reduced cell deformability [26,27]. Such cellular changes impact blood flow in narrow vessels, ultimately causing a transient or persistent blockage [28]. Three major causes of impaired blood flow have been identified as: (i) altered sickle cell rheology, (ii) inflammation, and (iii) cell adhesion; importantly, the latter two aspects are likely arising at least in part because of the first aspect [29-31]. The competition between the delay time for HbS polymerization and the RBC transit time in microcirculation is likely a key determinant of disease severity [32].

FIG. 1A is a schematic diagram depicting HbS polymerization which is the fundamental mechanism of SCD pathophysiology. Sickle cells (containing high HbS content) become rigid under low $O_2$ tension, increasing blood viscosity; when delay time (Ta) of HbS polymerization is shorter than RBC transit time (Tt), those rigid, sickled cells cannot escape microcirculation, leading to occlusion in post-capillary venules. HU and current gene-therapy trials can diminish HbS by elevated production of HbF; thus, extend the delay time of HbS polymerization, Td and retain cell deformability. FIG. 1B shows an example microfluidic impedance sensor 101 that provides sickle cell rheological measurement under controlled $PaO_2$ and in real-time in accordance with certain embodiments described herein.

Primary Innovations to Address Sickle Cell Disease Treatment and Pain Management Embodiments of the present disclosure provide on-chip dual-level $PaO_2$ control which enables clinically meaningful assessment of sickle cell functions. Polymerization of deoxygenated hemoglobin S (HbS) is the fundamental pathophysiological mechanism of sickle cell disease (SCD). Vasoocclusion events can be through the vascular tree, occurring from postcapillary venules of low oxygen tension (~20 millimetres of mercury (mm Hg)) to large cerebral arteries of high oxygen tension (~65 mm Hg). The proposed on-chip $O_2$ control replicates the blood gaseous environment transition in the in vivo vaso-occlusion sites. The measurements of $O_2$-dependent functional properties of sickle cells provide quantitative assessments of hematological outcomes that are directly associated with painful sickle cell vasoocclusion, for example, as a tool to predict pain crisis, and to evaluate the efficacy and patient response to pharmaceutical and gene-based therapies, and guide physicians to develop patient-specific treatment plan, as there is currently no microfluidic assay approved by the United States Food and Drug Administration (FDA).

In some implementations, a μZAS system integration towards a fully automated, rapid blood-to-results assay for sickle cell functional properties from 1-10 μL whole blood within <10 min is provided. Innovations relevant to address the low usability (as seen widely in microfluidic devices) include: (a) Operation of the microfluidic assays are compatible with standard micropipette operation for loading finger prick volume of blood specimens directly into the inlet of the microfluidic chips. (b) A magnetic force enabled snap fit module allows quick electrical connection between the disposable microfluidic chips and the instrument. (c) To drive the blood flow in the microfluidic devices, the gravity driven flow module is implemented in two possible simple designs: (i) titling the microfluidic chip at a specific angle to induce the flow or level to stop the flow, (ii) raising or lowering the water column that is connected to the outlet of the microfluidic chip to reduce or increase the flow rate. In either design, the motion is controlled by the embedded program of the instrument. This simple yet novel gravity-driven flow control strategy is able to eliminate the need for an external pump, needle, or tubing. (d) The pre-programmed instrument streamlines the control of $PaO_2$ transition, blood flow, and impedance monitoring, leading to a fully automated assay. The program also analyze the data and report the final results in a monitor.

Although the examples described herein primarily describe sickle cell disease, this technology can be used to test in general for the blood functions under oxygen conditions matching in vivo blood circulation or in extreme hypoxia or hyperoxia.

Example #1: it is known that in type 2 diabetes mellitus, blood flow is retarded, which can directly reduce the delivery of oxygen, insulin, and glucose to active tissues. The oxygen-dependent blood rheology measurement can be useful biophysical marker of diabetes.

Example #2: this technology can be used to assess whether blood flow is normal under hypoxia or evaluate dosage-dependences of blood flow on supplements or medications (e.g., sports medicine).

Microfluidic devices have shown great promise to assess various key aspects of sickle cell pathophysiological processes, including sickle cell deformability, morphology, adhesion, blood viscosity, and vaso-occlusion. However, these technologies have not been adopted widely because the low usability and low throughput are two major barriers to their clinical use. Existing microfluidics-based sickle cell assays are highly customized, limited to one blood testing at a time and up to a single $PaO_2$ condition. They typically require sophisticated infrastructure to support microfluidic testing, such as optical microscope, pressure pumps for blood flow control, and computers. These microfluidic innovations are often subjected to cumbersome operation (e.g., microbore tubing connections, syringe etc.) and incompatible with standard micropipette operation. These demands in microfluidic operation and testing intrinsically undermines its potential in high throughput assay. In addition, many microfluidic assays rely heavily on optical microscopy for cell morphological analysis, particle tracking (e.g., particle imaging velocimetry, PIV) for cell deformability or blood viscosity characterization, fluorescence labels for differentiation etc. Sophisticated image/video processing algorithms add additional computational and labor burdens to these microfluidic innovations.

Embodiments of the present disclosure use electrical impedance (denoted as "Z" herein) to replace optical microscopy for real-time measurements of cell rheology (deformability and microvascular occlusion) in microfluidic mimics of capillary structures. On-chip $PaO_2$ control for impedance measurement of sickle cells is achieved through microfluidic innovation which utilizes gas permeability of thin PDMS film (150 μm thick) that enables rapid diffusion (<15 s) of $O_2$ at a specific $PaO_2$ value from the gas channel to the cell channel. This approach enables characterization of alterations in sickle cell rheology, a cell function directly associated with HbS polymerization using ultrasmall volume of blood specimens. For example, real part of Z (R time series data) can be used to differentiate blood flow of normal cells from sickle cells, because occlusion induced by rigid sickle cells and those undergoing cell sickling events from HbS polymerization under low $PaO_2$ can largely increase the overall resistance to electric currents.

Quantitative evaluation of therapeutic efficacy in SCD treatment remains deficient. Therapeutic interventions, such as hydroxyurca (HU, FDA-approved drug) can ameliorate the polymerization process of deoxygenated HbS by elevated production of fetal hemoglobin (HbF), which can extend the delay time of HbS polymerization and thus cell sickling events and sickle cell rheology, improve the chance of sickle cells flowing well through microcirculation [33-37]. However, individual patient's hematological and clinical response to HU is quite variable, e.g., HbF level in some patients can be up to 40% [38]. Many patients have clinically meaningful increases in Hb F and declines in disease severity whereas some patients have little benefit. Nevertheless, in some patients even with high HbF levels, acute painful episodes and other symptoms still occur [39,40]. Anti-sickling modulators, e.g., Oxbryta® (voxelotor2) can increase the oxygen affinity of Hb, which can increase the cellular resistance to sickling. Besides hematopoietic stem cell transplantation, gene therapies [41-43] such as globin gene addition, gene editing to correct the SCD mutation, and genetic manipulations to enhance HbF production, may provide a cure to SCD than the pharmacological effects by HU but are still experimental.

Current assessment of treatment efficacy relies largely on patients reported outcomes, for example, pain frequency/scale, which are deficient and subjective. Conventional hematological and biochemical assays, such as complete cell count (CBC), high-pressure liquid chromatography (HPLC) and electrophoresis have limitations in the information they provide. It is known that HbF does not equally protect all RBCs from sickling damage, as heterogencities exist in cellular expressions of HbS and HbF [16]. Therefore, these hemoglobin assays are limited in providing mean corpuscular Hb concentration and percentages of Hb variants in hemolysate, which averages out the behavior of millions of cells. Cell morphology assays, such as F-cell counting, which can be measured via anti-HbF antibody, only offer an indirect measurement for the assessment of risk in abnormal blood rheology and sickle cell vaso-occlusion [16,44]. Therefore, functional measurements of sickle cells for their 02-dependent properties that are directly associated with the fundamental mechanism of the sickle cell pathophysiology (i.e., HbS polymerization), can serve as quantitative biophysical markers useful for close monitoring of patient response to therapeutic treatments as well as for recognizing a reasonable endpoint for gene therapies.

New assay technologies for sickle cell $O_2$-dependent function measurement are necessary. Current techniques for sickle cell measurements, such as cell deformability or morphological sickling assays do not provide sufficient resolution to dissect the complexity involved in $O_2$-dependent cell functions, or they are expensive, time-consuming and require sophisticated infrastructure to support the testing as well as highly skilled personnel for sample preparation, operation, and data interpretation. These limitations prevent them from being widely adopted for routine clinical, laboratory use. In vitro cell sickling assay using test tubes and membrane fixation (e.g., glutaraldehyde) for microscopic imaging, usually requires large sample volumes (~ mL) and long processing time (~ hr) 45. Cell imaging-based flow cytometry study of cell sickling in F-cells relies on image analysis and/or fluorescence labeling, which can be time consuming and technical demanding. Cell deformability assays, such as ektacytometry is useful to measure the degree of distortion of RBCs subjected to shear stress or varied osmotic pressures, using the method of laser diffraction viscometry. However, interpretation of cellular deformability is difficult when measuring heterogenous SCD blood, as it is challenging to properly align rigid and distorted sickle cells with the shear flow, resulting in a distorted diffraction pattern marked by an exaggerated decrease in apparent deformability.

Major barriers in clinical use of microfluidic assays and proposed method. In the past few decades, microfluidics-based devices have shown great promise to assess various key aspects of sickle cell pathophysiological processes, including sickle cell deformability [16,47,48] morphology [16,49] adhesion [50], blood viscosity [51], and vaso-occlusion [16,52]. Although these studies have revealed extreme heterogencities in sickle blood and significantly advanced our understanding of the fundamental mechanisms of sickle cell vasoocclusion, these technologies have not yet been adopted by the clinical use. Low usability is a major barrier for their clinical adoption. Existing microfluidic sickle cell assays are limited to blood testing under a single $PaO_2$ condition, and require sophisticated infrastructure to support microfluidic testing, which typically include optical microscope, computer, syringes, pumps for blood flow control. These microfluidic innovations are often subjected to cumbersome operation and incompatible with standard biomaterial operation (e.g., blood specimens need to be injected into the microfluidic device using needles, syringes and microbore tubing), thus performed poorly when operated by one without microfluidic trainings. In addition, many assays rely heavily on optical microscopy for cell morphological analysis, particle tracking (e.g., particle imaging velocimetry, PIV) for cell deformability or blood viscosity characterization, fluorescence labels for differentiation etc. These limitations in addition to the sophisticated imaging/video processing algorithms add additional computational/labor burdens to the use of these microfluidic innovations.

To bridge the gap, embodiments of the present disclosure provide a portable, easy-to-use, and automated micro electrical impedance-based assay system (μZAS) that provides rapid (<10 min) and accurate measurement of $O_2$-dependent sickle cell functional properties from ultrasmall volume (1-10 μL) of whole blood. Measurements include: (i) Š, sickling index of the cell sickling events, including the rate of cell sickling and fraction of sickled cells induced by intracellular HbS polymerization, and (ii) Ř, rheological index of sickle cell deformability and obstruction in micro-slits (rate and fraction of occlusion). Both functional measurements of sickle cells will provide quantitative assessments of key aspects of sickle cell pathophysiology, originated from the sickle cell mutation, and currently treated by pharmaceutics (e.g., HU, anti-sickling modulators).

Rigor of prior research. The proposed μZAS is built upon our SCD study in the past 10 years, published results [7,20,23,49,53-59] three patents [60-62] as well as the results in the literature. Our published work includes the designs of the microfluidic devices, electrical impedance for sickle cell detection and characterization, on-chip $PaO_2$ control, the portable electrical impedance measurement device, as well as the proof-of-the-concept results on both normal and sickle cell blood specimens.

We have developed a microfluidic approach for measurement of sickle cell properties under controlled $O_2$ environment (U.S. patent application Ser. No. 15/533,277) (see FIG. 4A). This approach directly measures changes in sickle cell functional properties induced by HbS polymerization, including kinetics of cell sickling and sickle cell rheology using ultrasmall volume of blood specimens [22,49,63]. This approach relies on microscopic imaging for quantification of cell and blood behaviors, as most other microfluidics-based cell assays do. To overcome this limitation, we have invented micro electrical impedance assay technologies (U.S. patent application Ser. No. 16/585,897, U.S. patent application Ser. No. 17/313,235) [61,62] that convert optical signals of sickle cell characteristics into electrical signals, enabling real-time, sensitive, and automated quantitative analyses of sickle cell blood under controlled $O_2$ environment.

Example Micro-Electrical Impedance-Based Assay System

FIG. 2A is a schematic diagram depicting an example micro-electrical impedance-based assay system 200 (e.g., pre-programmed instrument) that can be used for real-time monitoring of cellular response to environmental conditions (e.g., $PaO_2$ transition). As depicted, the system 200 includes a microfluidic device 202 (e.g., z-plate) comprising a plurality of microfluidic impedance sensors. The microfluidic device 202 further includes a cell channel configured to receive a sample substance and at least one gas channel operatively coupled to the cell channel defining a controlled testing environment of the microfluidic device 202. The at least one gas channel can define a gas channel network configured to supply different gaseous substances (e.g., oxygen at different concentrations).

In some implementations, the microfluidic device 202 comprises sixteen or more microfluidic impedance sensors. The plurality of microfluidic impedance sensors are configured to obtain, via one or more detection electrodes, electrical impedance-based measurement values with respect to the sample substance (e.g., blood). In various implementations, the microfluidic device 202 can include less than sixteen (e.g., four, eight, or twelve) microfluidic impedance sensors, or more than sixteen (e.g., twenty, twenty four, or twenty eight) microfluidic impedance sensors.

The system 200 can be configured for automated impedance measurement of oxygen dependent properties of sickle cells. In some implementations, the microfluidic device 202 and/or the plurality of microfluidic impedance sensors is integrated into the system 200 (e.g., instrument) via a push-fit and/or rocker module as discussed in connection with FIG. 9A, FIG. 9B, and FIG. 10B below. This design facilitates a dual-level $PaO_2$ control, through a single inlet (gas supplies sequenced by a 3-way valve) and a single outlet (open to air), while providing independent impedance measurement of, in some examples, 16 cell channels without cross-talking.

In some implementations, the system 200 uses a gravity-driven flow control strategy to tilt the microfluidic device 202 (e.g., z-plate) including the plurality of microfluidic impedance sensors (e.g., positioned within a gas channel network) to improve the accuracy of the impedance measurement of a sample substance (e.g., blood specimen). For example, the system can include a gravity driven flow module configured to generate a gravity-driven hystatic pressure difference to drive a flow of the sample substance through the one microfluidic device 202. In some implementations, automated blood-to-results assay is achieved through the embedded program that streamlines $PaO_2$ transition from multiple channels, such as a first testing gaseous substance 205A (e.g., oxygen atmospheric to 65 mm Hg) and a second testing gaseous substance 205B (e.g., oxygen atmospheric to 20 mm Hg), for example, via a 3-way gas valve.

A measurement instrument and/or controller can be operatively coupled to the microfluidic device 202 to control the testing environment. For example, the measurement instrument and/or controller can be configured to determine and output at least one measurement value in relation to the sample substance to provide quantitative assessment of a hematological condition or outcome (e.g., determine at least one of a sickling index and/or sickle cell rheology). In some examples, a change in electrical impedance above a predetermined threshold detected by the controller is indicative of an abnormal blood flow. The controller can be configured to detect a $PaO_2$ transition resulting from resistance to electric currents associated with a corresponding sickling event. In some examples, the measurement instrument/controller are configured to measure a rate of blood flow through the microfluidic device 202. An example microfluidic device 202 can include at least one microstructure (e.g., a plurality of micro-slits) for measuring a flow condition or obstruction.

FIG. 2B illustrates program $PaO_2$ control and impedance monitoring.

FIG. 2C is a diagram of the proposed microcontroller-relay system 250 for impedance monitoring. As illustrated in FIG. 2C, an example system can include one or more microcontrollers, a 2-channel relay module, AD5933 impedance converter chips, a tilting stage with pogo-pin printed circuit board (PCB) lid, solenoid valve (normally closed), and monitor packaged into an electromechanical housing. The 2-channel relay module can be pre-programmed to streamline gas valve and AD5933 chips.

Figure 3:
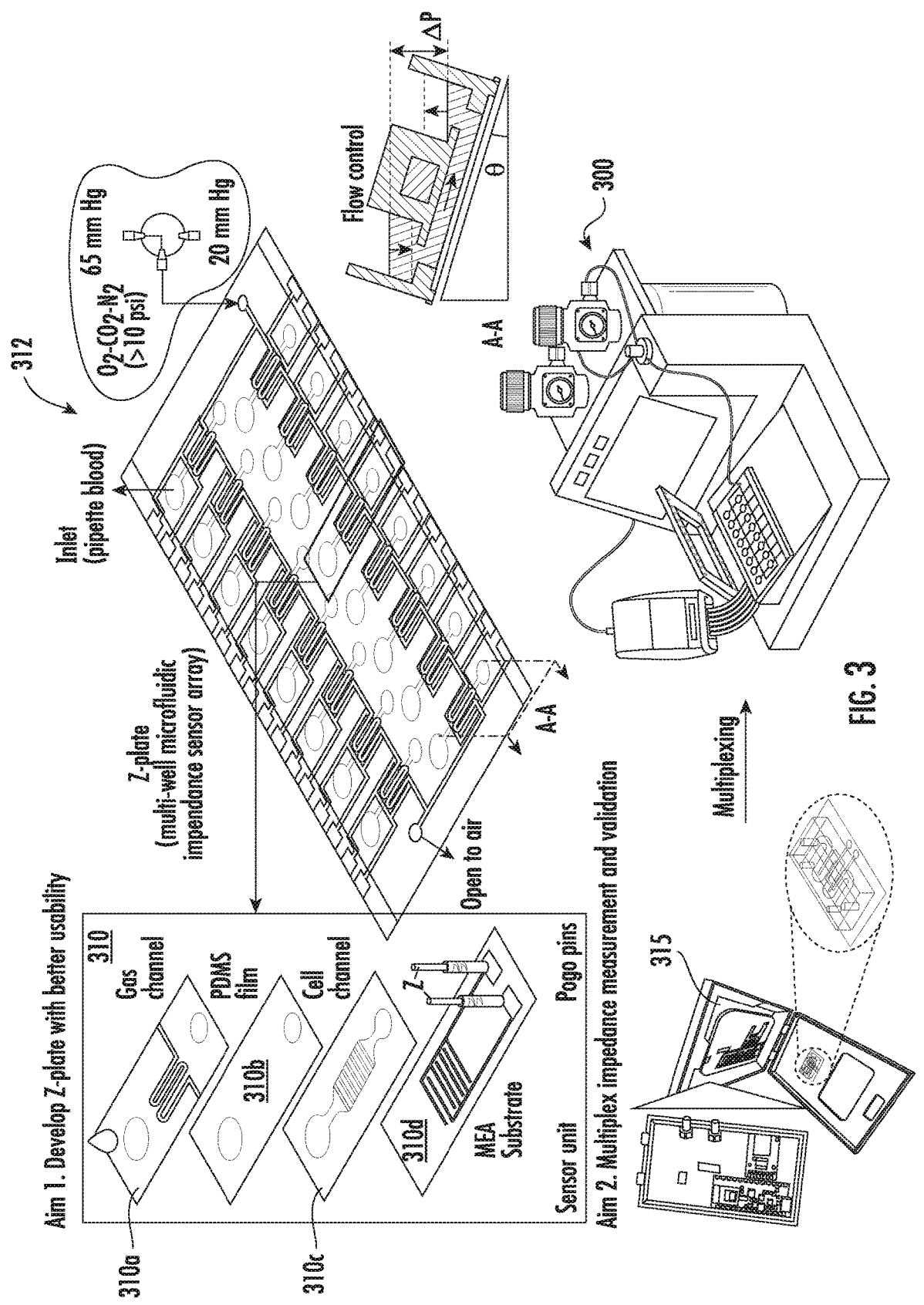
FIG. 3 depicts a Microfluidic Impedance Sensor Array System ($\mu$Z-SAS) in accordance with embodiments of the present disclosure.

FIG. 3 is a schematic diagram depicting a Microfluidic Impedance Sensor Array System (µZ-SAS) 300 in accordance with embodiments of the present disclosure that provides rapid (<10 min), high throughput, and accurate measurement of $O_2$-dependent sickle cell rheology from ultrasmall volume (10-50 µL) of whole blood. The example µZ-SAS 300 consists of a Z-plate 312, a multi-well microfluidic impedance sensor array comprising a plurality of sensor units 310 and a preprogrammed instrument for multiplexed impedance measurement 315. The Z-plate 312 can comprise a plurality of (e.g., sixteen or more) independent microfluidic impedance sensors (e.g., sensor unit 310) for high throughput rheological measurement of sickle cells (deformability and obstruction in micro-slits) under a dual-level $PaO_2$.

As depicted in FIG. 3, the sensor array (e.g., each sensor unit 310) can include a top gas channel network (310a), providing physiological $PaO_2$ control for all cell channels (310c) underneath a gas permeable Polydimethylsiloxane (PDMS) film (310b), through low-pressure (<10 psi) supplies of two $PaO_2$ (20 mm Hg and 65 mm Hg). In some implementations, transition of $PaO_2$ is conducted by a programmable 3-way valve. A multielectrode array (MEA) (310d) is used to provide independent impedance measurement of blood specimens in each cell channel with no cross-talking. In some implementations, a novel gravity-driven flow strategy is used to create a hydrostatic pressure, $\Delta P$ at a tilt angle, $\theta$, driving the blood flow without the need of microbore tubing or external pumping action (FIG. 3, A-A). The measurement instrument 315 is further developed by multiplexing for real-time monitoring of 16 microfluidic devices. This functional measurement of sickle cell rheology can provide quantitative assessments of key aspects of the sickle cell mutation (HbS) and currently treated by pharmaceutics (e.g., Hydroxyurca (HU), antisickling modulators) and gene-therapies.

Figures 4A, 4B, 4C, 4D, 4E:
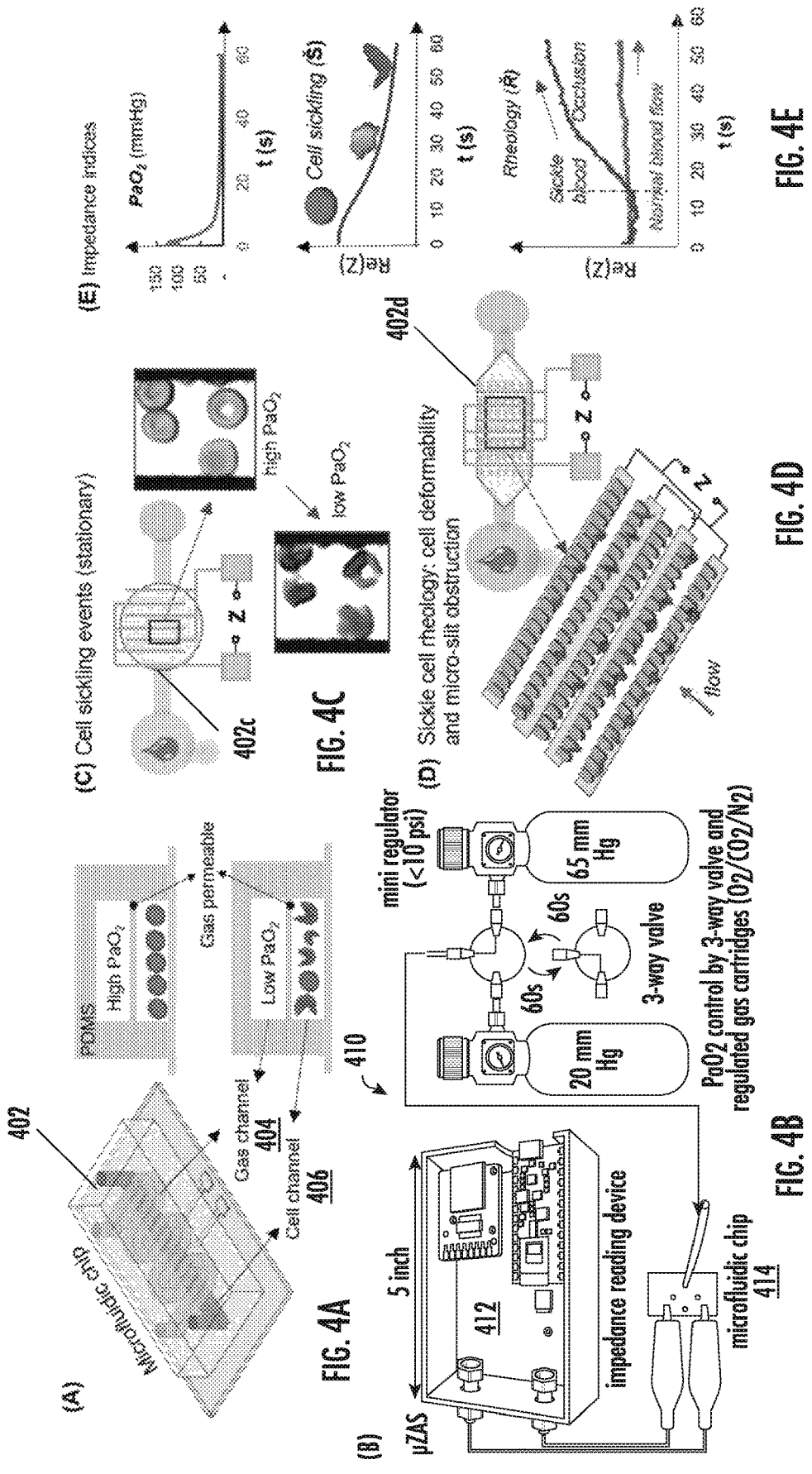
FIG. 4A depicts a microfluidic impedance chip in accordance with certain embodiments described herein.
FIG. 4B depicts a prototype of a Micro-Electrical Impedance-Based Assay System ($\mu$ZAS) in accordance with certain embodiments described herein.
FIG. 4C is a schematic diagram illustrating a microfluidic chip for cell sickling measurement under stationary condition in accordance with certain embodiments described herein.
FIG. 4D is a schematic diagram illustrating a microfluidic chip with arrays of micro-slits for sickle cell rheology measurement in flow condition in accordance with certain embodiments described herein.
FIG. 4E are graphs depicting a representative case of impedance monitoring of cell sickling events and sickle cell rheology.

FIG. 4A depicts a microfluidic impedance chip 402 in accordance with certain embodiments described herein. The microfluidic impedance chip 402 enables real-time monitoring of cellular response to $PaO_2$ transition, which is achieved with a double-layer PDMS structure for on-chip gas environmental control. $O_2$-dependent sickle cell function measurement with µZAS. As shown, the example microfluidic impedance chip 402 includes at least one gas channel 404 and at least one cell channel 406.

FIG. 4B depicts a prototype of µZAS 410 consisting of a handheld impedance reading device 412 and disposable microfluidic chips 414 with one inlet of gas channel connected to a 3-way valve accepting $PaO_2$-defined supply from portable gas cartridges, as well as a graphical user interface (GUI) (not shown). In some implementations, a display device or monitor operatively coupled to the µZAS and the controller configured to output at least a portion of the electrical impedance-based measurement values. In various implementations, the electrical impedance-based measurement values can be used to evaluate treatment efficacy for sickle cell disease, determine a biophysical marker of diabetes, assess whether blood flow is normal under hypoxia, or to evaluate dosage-dependencies of blood flow on medications.

FIG. 4C is a schematic diagram illustrating a microfluidic chip 402c for cell sickling measurement under stationary condition.

FIG. 4D is a schematic diagram illustrating a microfluidic chip 402d with arrays of micro-slits for sickle cell rheology measurement in flow condition (only cell channel is illustrated).

FIG. 4E are graphs depicting a representative case of impedance monitoring of cell sickling events and sickle cell rheology.

Embodiments of the present disclosure provide a µZAS with enhanced usability, sensitivity, and specificity through the innovative aspects as follows:

1) On-chip dual-level PaO$_2$ control enables clinically meaningful assessment of sickle cell functions. Polymerization of deoxygenated HbS is the fundamental pathophysiological mechanism of SCD. Vasoocclusion events can be through the vascular tree, occurring from postcapillary venules [64,65] of low oxygen tension (~20 mm Hg) to large cerebral arteries [66,67] of high oxygen tension (~65 mm Hg). The proposed on-chip O$_2$ control replicates the blood gaseous environment transition in the in vivo vaso-occlusion sites (FIG. 4B). The measurements of O$_2$-dependent functional properties of sickle cells provide a comprehensive, quantitative assessment of key aspects of the fundamental mechanism of SCD pathology as well as the hematological outcomes that are directly associated with HbS (or its O$_2$ affinity) and treated by pharmaceutical and gene-based therapies.

2) Integration of electrical impedance sensing with on-chip oxygen control into microfluidic devices enables label-free detection of functional properties that are specific to sickle cells. The electrical impedance signal is inherently digital, which can be processed quickly using our existing script (in MATLAB) in less than 1 minute. Although electrical impedance itself is non-specific, the proposed assay via the on-chip O$_2$ tension control makes it specific to sickle cells because of cellular alterations being directly caused by HbS polymerization, for example, cell sickling events and micro-slit obstruction (FIGS. 4C-E).

3) μZAS system integration towards a fully automated, rapid blood-to-results assay for sickle cell functional properties from 1-10 μL whole blood within <10 min. Operation of the microfluidic assays are compatible with standard micropipette operation for loading blood specimens. A push-fit module enables quick electrical connection between the disposable microfluidic chip and the instrument. A novel gravity-driven flow control strategy is introduced to eliminate the need for an external pump. The pre-programmed instrument streamlines the control of PaO$_2$ transition, blood flow, and impedance monitoring, leading to a fully automated assay.

Experimental Results and Examples

A study was conducted to develop and evaluate the exemplary system and method comprising microfluidic assays of sickle cell functional properties to provide quantitative assessments of disease heterogeneity and severity. A microfluidic strategy for on-chip O$_2$ control was developed, which is critical to measure O$_2$-dependent sickle cell functional properties. This method utilizes gas permeability of thin PDMS film (~150 μm thick) that enables rapid diffusion of O$_2$ at a specific PaO$_2$ value from the gas channel to the cell channel. Measurements of kinetics of cell sickling and the sickle cell rheology (i.e., deformability change and obstruction at micro-slits) are achieved using cell-imaging analysis. In a pilot study on 25 SCD patients with HbS level of 64.0-90.1%, we have demonstrated that both kinetics of cell sickling (e.g. sickled fraction-sickling events count/total cell count) and sickle cell rheology (capillary occlusion) can be used as biophysical markers of SCD severity [20].

Figures 5A, 5B, 5C, 5D:
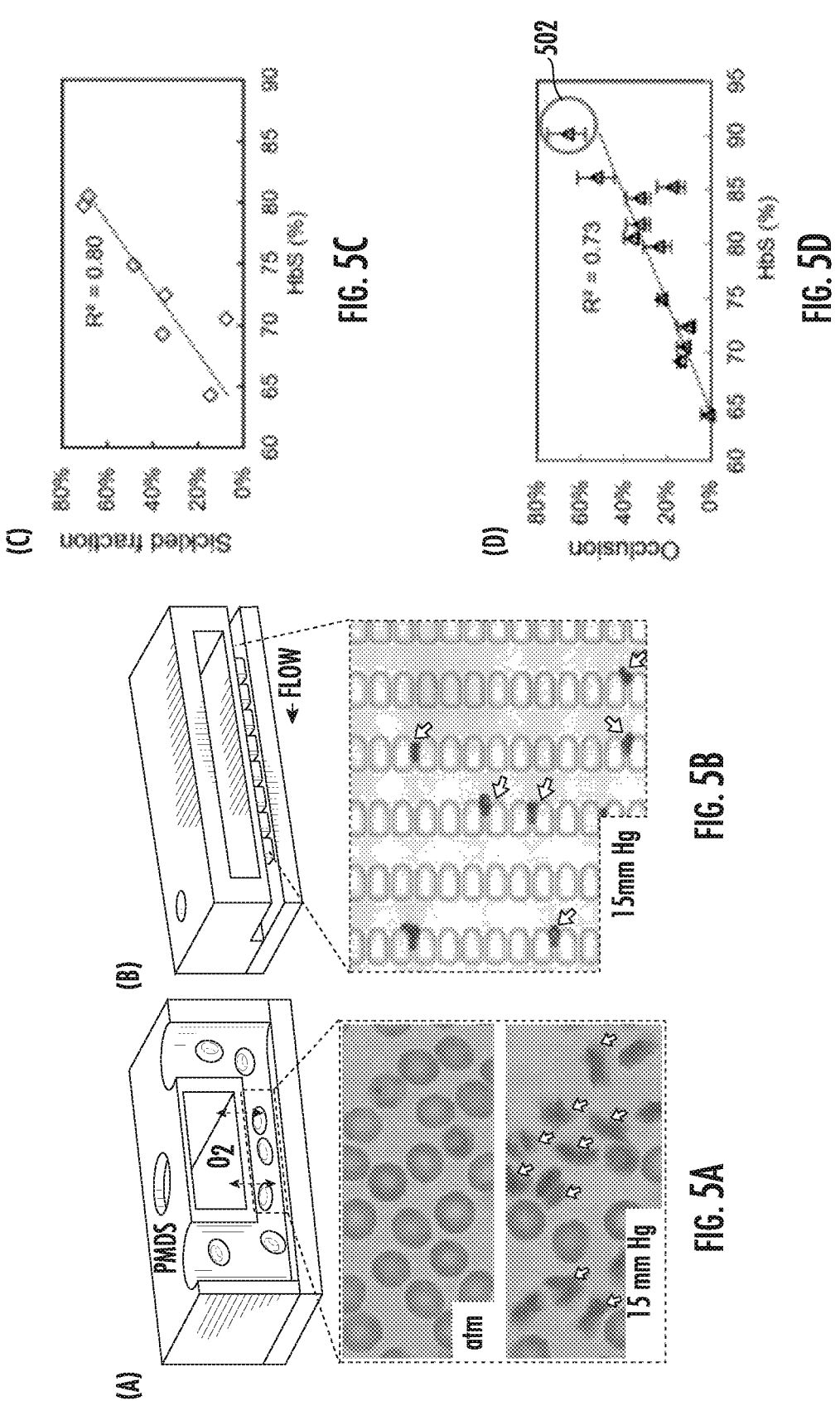
FIG. 5A illustrates cell sickling events induced by low $O_2$ tension.
FIG. 5B illustrates sickle cells containing rigid HbS fibers.
FIG. 5C is a graph depicting strong linear regression between sickled fraction (fraction of cells undergoing cell sickling) and patient's HbS level obtained from HPLC.
FIG. 5D is a graph depicting strong linear regression between micro-slit obstruction and patient's HbS level.

FIG. 5A illustrates cell sickling events induced by low O$_2$ tension. Red arrows are sickled cells with irregular morphologies. FIG. 5B illustrates sickle cells containing rigid HbS fibers obstruct the micro-slits in the channel. FIG. 5C is a graph depicting strong linear regression between sickled fraction (fraction of cells undergoing cell sickling) and patient's HbS level obtained from HPLC. FIG. 5D is a graph depicting strong linear regression between micro-slit obstruction and patient's HbS level. Red circled (502)— diagnosed as a severe case.

Cell sickling events induced by exposing sickle cells to a transient hypoxia (e.g., reduce the atmospheric (atm) PaO$_2$ to a low O$_2$ tension level) are measured under stationary condition (FIG. 5A). Intracellular HbS polymerization leads to irregular cell shape, which can be identified under microscope. Sickle cell rheology (deformability and occlusion) are measured under flow condition for 60 s, where sickle cells with extended delay time in HbS polymerization can escape the micro-slits but those containing rigid HbS fibers (undissolved HbS or hypoxia induced HbS fibers) lose their deformability and become trapped at the micro-slits (FIG. 5B). These two aspects of sickle cell behavior measured under controlled O$_2$ tension (in exposure to testing PaO$_2$ 15 mm Hg briefly for 60 s) provided quantitative cell functional assessment, which show strong linear correlation to patient's HbS level, as obtained from standard HPLC (FIG. 5C and FIG. 5D). In addition, heterogeneities in the sickle cell functional properties reflect the heterogeneous distribution of intracellular HbS/A/F and water content, which cannot be measured with standard methods, such as electrophoresis or HPLC.

Sickle cell functional properties are useful to assess the efficacy of drug treatment. Quantification of sickle cell functional properties under a physiological O$_2$ tension, e.g., 15 mm Hg as seen in capillary bed, has been demonstrated useful to assess the efficacy of HU to SCD in our pilot study [20,75].

Figures 6A, 6B, 6C, 6D, 7A, 7B, 7C:
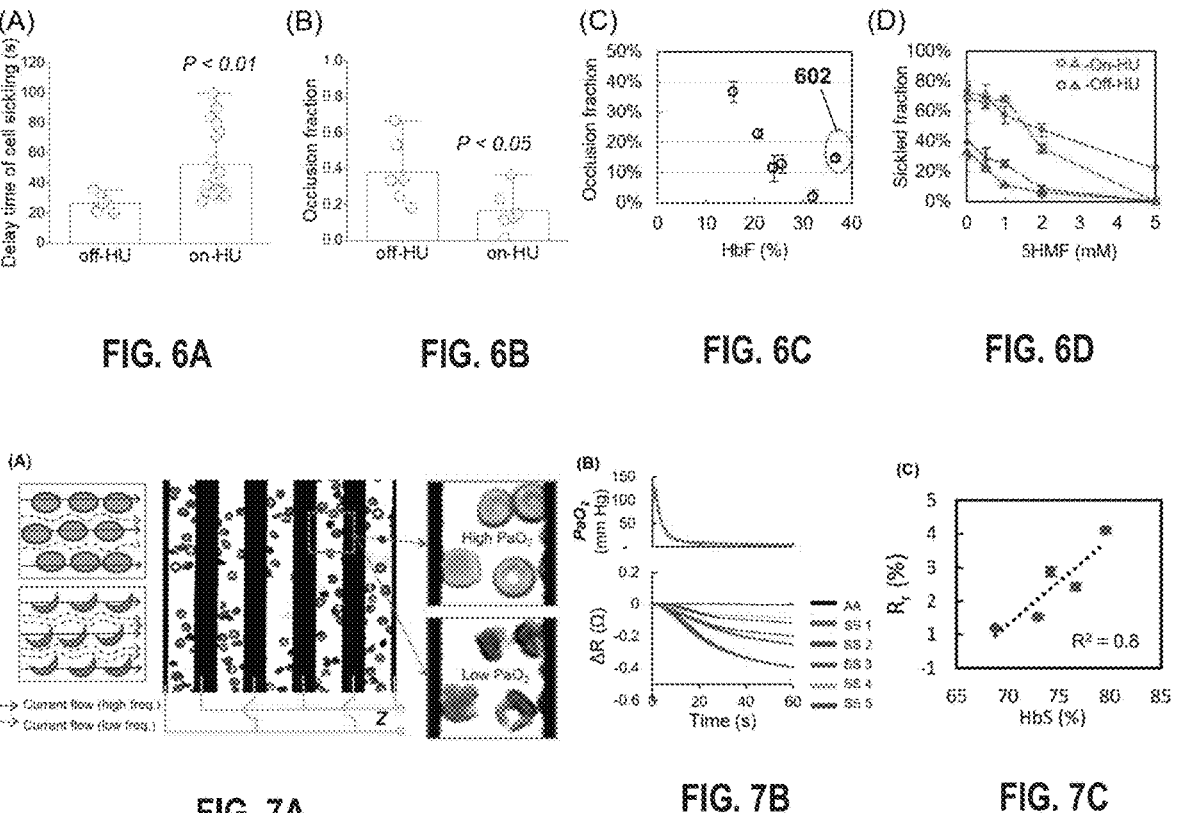
FIG. 6A demonstrates that hydroxyurea (HU) significantly extended the delay time of cell sickling, which ameliorates the clinical symptoms in patients accepting HU treatment.
FIG. 6B demonstrates that sickle cells from patients accepting HU treatment have much less obstruction in micro-slits.
FIG. 6C illustrates sickle cell rheology (occlusion) showing patient-specific response to HU treatment.
FIG. 6D shows a patient-specific response to Hydroxyurea (HU) and $O_2$ affinity modulator (5HMF).
FIG. 7A demonstrates that when $PaO_2$ drops, resistance to electric currents decreases along with cell sickling events because of HbS polymerization and reduction in surface area of sickled cells.
FIG. 7B are graphs showing that collective behavior of Red Blood Cells (RBCs) is monitored by the decreased impedance.
FIG. 7C is a graph demonstrating impedance analysis of homozygous sickle cell specimens shows strong correlation with patients' HbS levels.

FIG. 6A-6D are graphs depicting sickle cell functional properties for assessment of efficacy of pharmaceutical treatments, e.g., Hydroxyurca (HU) and O$_2$ affinity modulator (5HMF). FIG. 6A demonstrates that HU (red symbols, "on-HU") significantly extended the delay time of cell sickling, which ameliorates the clinical symptoms in patients accepting HU treatment. FIG. 6B demonstrates that sickle cells from patients accepting HU treatment have much less obstruction in micro-slits. FIG. 6C illustrates sickle cell rheology (occlusion) showing patient-specific response to HU treatment, where patient with high HbF level can still have high occlusion fraction (red circle, 602). FIG. 6D shows a patient-specific response to 5HMF.

Our results showed that HU treatment significantly extended the delay time of cell sickling events (FIG. 6A), which is critical in that most of sickle cells can have time to escape the microcirculation before they become rigid (sickled, due to HbS polymers). This effect has also been demonstrated in our in vitro assay of sickle cell rheology, where patients with HU treatment showed much less occlusion fraction (FIG. 6B). Both measurements showed that HU treatment by elevated production of HbF can ameliorate HbS polymerization and clinical symptoms. It is known that patient's response to HU treatment vary significantly, with large variation (15.7%-36.9%) in the distribution of HbF level among different patients (FIG. 6C). Our in vitro microfluidic assay (e.g., sickle cell occlusion) shows a moderate correlation (R2=0.6) between occlusion fraction and HbF level. Importantly, the occlusion testing showed that a blood sample of high HbF level can still have high occlusion fraction (red circle (602), FIG. 6C), which explains why in some patients even with high HbF levels, acute painful episodes and other symptoms still occur [39, 40]. This, however, could not be detected using conventional hematological assay, such as Hb electrophoresis or HPLC.

We further demonstrated that microfluidic assay offers a convenient tool to assess efficacy of anti-sickling oxygen modulator, 5-(hydroxymethyl) furfural-based anti-sickling drug (5HMF). The dosedependence is similar among 5 patients, but significant variations exist, indicating patient-specific response (FIG. 6D). These preliminary studies provided cell-level perspectives of the clinical manifestations in SCD patients and offered quantification of patient-specific responses to therapeutic treatments.

Electrical impedance replaces optical microscopy in real-time measurements of sickle cell functions. Analysis of sickle cell functional properties in microfluidic devices requires recording and processing microscopic video, which cannot be easily implemented for automated blood-to-results testing. Embodiments of the present disclosure use electrical impedance as an alternative method to optical microscopy. Electrical impedance is the opposition to alternating current presented by a circuit, denoted as $Z=R+iX$, where R is the real part and X is the imaginary part. Electrical impedance-based detection is inherently quantitative, non-invasive, and label-free, eliminating the needs for fluorescence or biochemical labeling, and data storage and processing in conventional microscopybased approach [88]. Electrical impedance has been widely used for real time measurements of cell spreading and proliferation [89, 90] as well as cellular/subcellular characterizations [74, 91-93]. We have demonstrated the capability of electrical impedance in detection of single sickle cells [7,59] cell sickling/unsickling process in response to transient hypoxia [56], and sickle cell capillary obstruction under controlled $O_2$ conditions [53].

FIGS. 7A-7C illustrate electrical impedance-based measurement of cell sickling events in real time. FIG. 7A demonstrates that when $PaO_2$ drops, resistance to electric currents decreases along with cell sickling events because of HbS polymerization and reduction in surface area of sickled cells (in microscopic photograph). FIG. 7B are graphs showing that collective behavior of RBCs is monitored by the decreased impedance (real part, R) where cell sickling events in sickle blood continue progressively while normal RBCs retain their surface areas and show no significant change. AA-normal, SS1-5 are 5 sickle cell patient samples. FIG. 7C is a graph demonstrating impedance analysis of 5 homozygous sickle cell specimens shows strong correlation with patients' HbS levels.

The well-established equivalent circuit model describes a biological cell using a membrane capacitor connected in series with an interior Hb resistor [91]. Cell sickling caused by the growth of deoxygenated-HbS fibers results in reduction in cell surface area and volume, decreasing the overall cellular opposition to electric currents (FIG. 7A). The decrease in the real part R of impedance obtained from our cell sickling microfluidic chip can provide a quantitative assessment of the cell sickling event in real time (FIG. 7B). Furthermore, based on our pilot study of 5 patient samples, the sickling index shows strong linear correlation ($R^2=0.8$) with patient's HbS level, showing similar sensitivity as imaging-based assay as shown FIG. 5C.

FIGS. 8A-8C illustrate validation of electrical impedance measurement of rheology by optical microscopy [53]. FIG. 8A illustrates steady flow of sickle cells under high $PaO_2$ and obstruction at micro-slits by rigid, sickled cells under fully deoxygenated condition. FIG. 8B is a graph showing real time impedance (real part, R) monitoring of cell rheology along when $PaO_2$ decreases to 0 mm Hg. FIG. 8C is a graph demonstrating strong linearity in sickle cell occlusion (time-dependent measurement) between impedance signal and microscopic analysis.

The equivalent circuit model can also well explain the electrical impedance-based detection of capillary obstruction by sickle cells (FIG. 8A). At high $PaO_2$ level (e.g., 133 mm Hg), majority of blood cells are deformable and can squeeze through micro-slits without significant obstruction events.

When the $O_2$ decreases, sickle cells lose their deformability due to the intracellular HbS fibers: those cells have short delay time of HbS polymerization cannot escape the microslits, leading to occlusion in the microfluidic device. As occlusion worsens, it increases the opposition to the electric currents, thus leading to an increase in electrical impedance, e.g., detected by the real part, R (FIG. 8B). In contrast, normal blood cells retain their deformability regardless of $O_2$ tension, therefore no change in impedance reflects a normal blood flow. We further determined the strong linear correlation between the impedance index of occlusion and the imaging-based occlusion analysis (FIG. 8C).

Most of microfluidic designs for impedance measurement as reported in literature requires soldering wires to the electrode pads or using alligator clips, which can result in variation due to inconsistency in contact impedance. To drive the blood flow, syringe pumps or air-pressure driven flow are often used, which require sophisticated microbore tubing connection and/or microneedles to access the microfluidic chip, leading to variation in measurements due to human error. In our proof-of-concept study, we implemented electrical impedance-based analyses of $O_2$-dependent cell sickling kinetics and $O_2$-dependent sickle cell rheology [53]. Although this implementation demonstrated the feasibility of blood-to-results assay using our developed portable impedance reading device, the operation of the example microfluidic device is not currently compatible with standard micropipette operation. This disclosure contemplates that these limitations can be addressed through two engineering innovations: (1) a push-fit module for quick electrical connection, and (2) a gravity-driven flow control strategy to simplify the microfluidic operation.

Example Push-Fit Module/Component

To improve the usability of the microfluidic assay, a push-fit module is employed to optimize the designs of microfluidic chips via computer modeling/simulation, and implement a gravity-driven flow strategy to control the blood flow in the device, so that the microfluidic testing is compatible with standard micropipette operations and does not require any external pumping action, microbore tubing or wire soldering. A prototype of a push-fit module was developed to further simplify the electrical connection between the disposable microfluidic chip and the testing instrument via standard BNC-SMA cable.

Figures 9A, 9B:
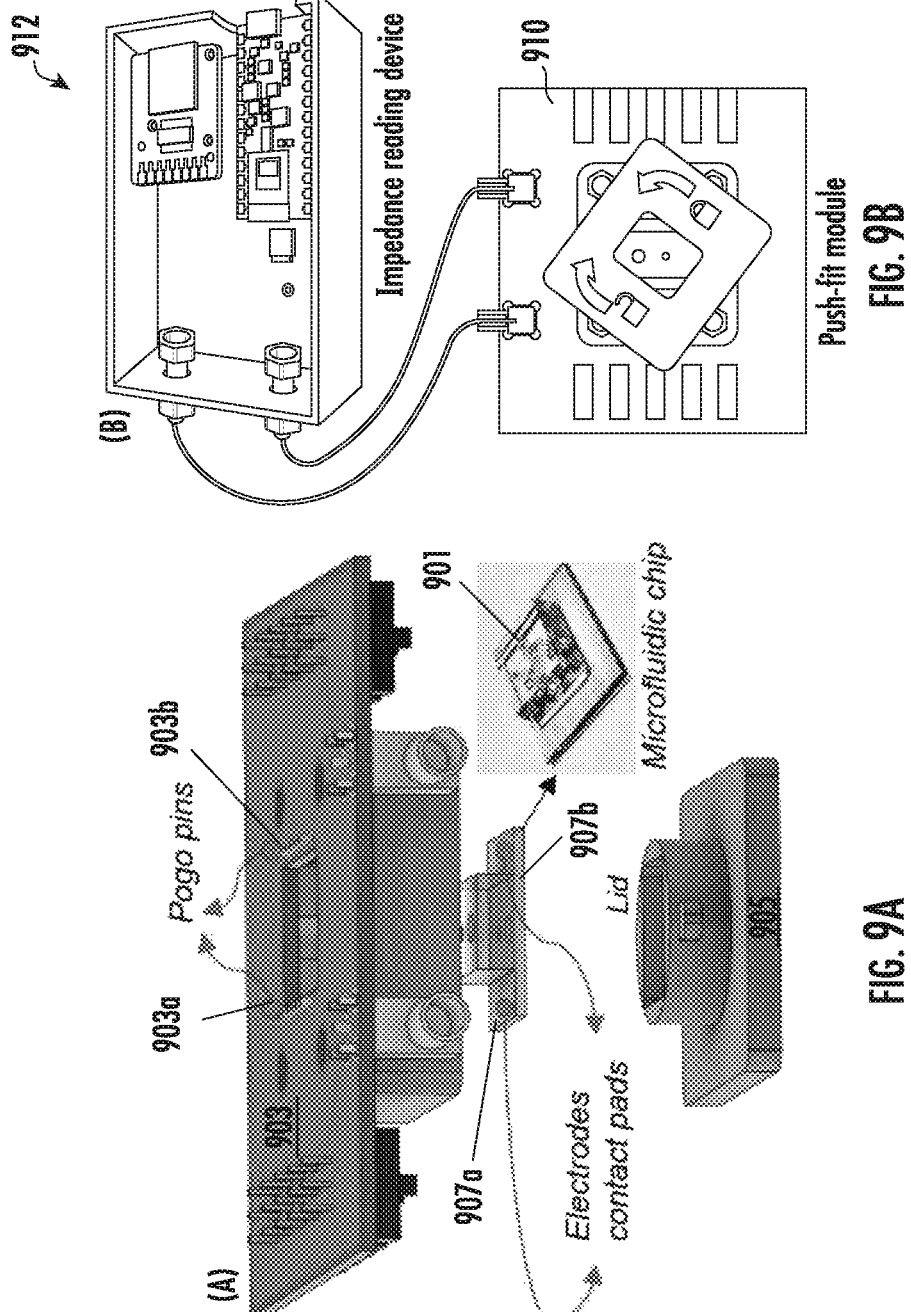
FIG. 9A depicts an example microfluidic chip in accordance with certain embodiments described herein.
FIG. 9B shows a push-fit module in accordance with certain embodiments described herein.

FIGS. 9A-9B are schematic diagrams showing an example push-fit module that enables quick electrical connection between a microfluidic chip and the impedance reading device. In some examples, a microfluidic device and an example measurement instrument (e.g., impedance reading device) are operatively coupled to one another via a magnetic, force, or snap-fit connection.

FIG. 9A shows an exploding view, where a microfluidic chip 901 is placed between the pogo pins-Printed Circuit Board (PCB) 903a, 903b and a resin lid 905. FIG. 9B shows a push-fit module 910 connected to a microcontroller 912 via standard BNC-SMA cable. The microfluidic chip 901 can be easily locked or unlocked by rotating the lid. In the example shown in FIG. 9B, the push-fit module 910 consists of a resin cap 905 and a PCB 903 with pre-soldered spring-loaded pogo pins (903*a*, 903*b*). Rotation of the resin cap 905 locks the microfluidic chip 901 and provides a firm electrical connection between the pogo pins (903*a*, 903*b*) and the electrode pads 907*a*, 907*b* on the microfluidic chip. This module significantly improves the usability of microfluidic devices and reduces the variation in impedance measurement associated with wire soldering.

Example Rocker Module for Programmable Gravity-Driven Flow Control

Figures 10A, 10B:
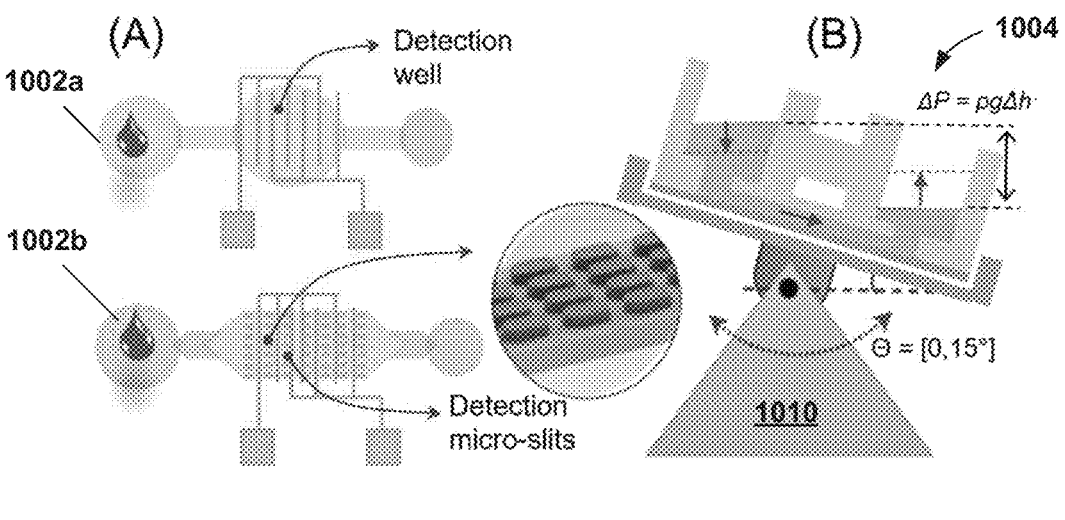
FIG. 10A depicts microfluidic devices for cell sickling assay and cell rheology assay in accordance with certain embodiments described herein.
FIG. 10B depicts an example programmable rocker for gravity-driven flow in accordance with certain embodiments described herein.

FIG. 10A depicts microfluidic devices (1002*a*, 1002*b*) for cell sickling assay (top, 1002*a*) that comprises a detection well and cell rheology assay (bottom, 1002*b*) that comprises detection micro-slits.

FIG. 10B depicts an example programmable rocker 1010 for gravity-driven flow. In some implementations, for the sickling assay (1002*a*), a large angle (e.g., between 15 degrees and 45 degrees) is used to quickly bring sickle cells to detection electrodes. In other implementations, for the rheology assay (1002*b*), a small angle (e.g., between 1 degree and 15 degrees) is used to induce a constant hydrostatic pressure difference, $\Delta p$ to drive blood flow.

To eliminate the external flow control equipment (such as a syringe pump or pressure pump) that is required to bring blood cells to the detection electrodes for impedance measurement at the detection well or micro-slits (FIG. 10A), a gravity-driven flow control strategy is implemented through a programmable 2D rocker (1010 shown in FIG. 10B). As shown in FIG. 10B, the microfluidic device 1004 is mounted on (e.g., removably attached to) the rocker 1010. This is similar to the concept of rocking utilized in cell culture or bioreactor systems. Design of microfluidic flow in the channel is based on the incompressible Navier-Stokes equation:

$$\rho\left[\frac{\partial U}{\partial t} + U \cdot \nabla U\right] = -\nabla P + \mu \Delta U + \rho g,$$

Where t is time, $\rho$ is the fluid density, U is the velocity vector field, $\mu$ is the fluid viscosity, P is the pressure, and g is the gravity vector. When the microfluidic chip (e.g., 1002) is tilted at a certain angle, $\theta$, it creates a hydrostatic pressure, $\Delta P = \rho g \Delta h$, to induce blood flow. This flow will be programmed differently for each assay.

This disclosure contemplates utilizing theoretical analysis and Multiphysics simulation to optimize the microfluidic architecture and dimensions. Current design of the disposable microfluidic chip consists of a double-layer polydimethylsiloxane (PDMS) structure, including a cell channel (5 $\mu$m deep), a gas channel (100 $\mu$m deep), and an in-between PDMS film (100-150 $\mu$m thick), allowing precisely $PaO_2$ and deoxygenation rate to induce cell sickling in the cell channel. Modifications of the microfluidic devices will be focused on cell channel in each assay. Fluidic access to cell channel is easily provided by a 3 mm opening (FIG. 10A), facilitating micropipette loading of blood specimens. Gas channel will be designed as symmetrical with one inlet connecting to the gas supply for $PaO_2$ control, via a 23-gauge blunt needle, while the outlet (1.5 mm diameter) open to air (FIG. 4A). A major difference between the cell sickling device and rheology device is the architecture of the cell channel, where the cell sickling assay is a simple straight channel with a detection well in the middle, while the rheology assay has rows of micro-slits in the detection well as illustrated in FIG. 10A and FIG. 10B.

In various implementations, design variables, including channel length, detection volume, interdigitated electrode band/gap, micro-slit dimensions and count (for rheology assay), as well as the angle $\theta$ will be determined from the numerical simulation of the coupled AC/DC (impedance) and computational fluid dynamics (CFD) in COMSOL Multiphysics Multiphysics environment. COMSOL (AC/DC module and microfluidics module) can be used for varied simulations of fluid flow [95,96] diffusion [97], and electrical impedance [98]. The physiological blood flow can be simulated as seen in similar sized small veins [99], by matching the wall shear stress value 1-6 dynes/cm$^2$ in the micro-slits for sickle cell rheology assay. Various microfabrication techniques can be utilized to fabricate the microfluidic devices, including silicon mold (such as photolithography and fluorinated silane vapor passivation), electrode deposition/patterning, replication procedure for casting PDMS channels, and plasma-enhanced device bonding.

Embodiments of the present disclosure provide optimized microfluidic devices according to various specifications:

Example #1

Microfluidic chips matching for standard sized microscope slides/cover slips

Example #2

Rapid transition (<20 s) to testing $PaO_2$ in the cell channel, e.g., from atmospheric level to a testing level.

Example #3

<5% flow variation (occlusion-free steady flow) within 5 mins by the gravity-driven flow control strategy in cell rheology assay.

Discussion

The most significant limitation in our preliminary study (including many other microfluidic studies reported in literature) was the sedimentation of blood cells at the inlet when the microfluidic chip was flattened for microscopy. This unnecessarily reduced the number of blood cells to flow towards the detection electrodes. The proposed gravity-driven flow by tilting the microfluidic chip at a specific angle can resolve this issue and largely improve the flow of blood cells for accurate impedance measurement of the blood specimen. In this regard, a potential issue may arise from the titling of the device: the pressure difference ($\Delta P$) can decrease as the flow continues, leading to a reduction in the water column height difference ($\Delta h$). Hence, it may interfere with the measurement of the rheology and occlusion index. However, a theoretical analysis based on our current prototype demonstrates such change is negligible. Considering the small cross-sectional area of the micro-slit (4 $\mu$m by 5 $\mu$m in our current prototype), the corresponding flow rate in the cell channel is of an order of $1 \times 10^{-4}$ $\mu$L/s at a physiological shear stress level 1 dynes/cm$^2$. For a continuous monitoring of 5 minutes, such ultrasmall flow rate leads to a total volume movement of 0.03 $\mu$L and a negligible variation of the water column height (13 $\mu$m) across inlet and outlet. Given the total length of channel is 15 mm and $\theta=15°$, the maximum variation in the driving pressure, $\Delta P$ is less than 0.1%. Hence, a constant hydrostatic pressure and a steady blood flow is guaranteed for a few minutes of measurement. Given the rare circumstance that the variation becomes not negligible, we will modify the design and/or operation, such as by increasing the volume ratio of the inlet reservoir over the microchannel and/or slightly shorten the testing time.

Most existing microfluidic designs, especially those with electrical-fluidic-gas coupling, require users to manually operate and interact with the control/testing system at specific timepoints. This largely lowers the usability of the microfluidics, especially by those who do not have sufficient training or engineering skills. Embodiments of the present disclosure provide an easy-to-use, fully automated blood-to-results assay that can be adopted widely for clinical practice and operated by non-engineers. The main instrument will be designed as a simple push-button-to-start measuring system. The program embedded in the instrument will perform the microfluidic testing and report the results from the specific assay without further user interaction, after the blood is loaded into the microfluidic device and gas supply tubing inserted.

Figures 11A, 11B, 11C, 11D:
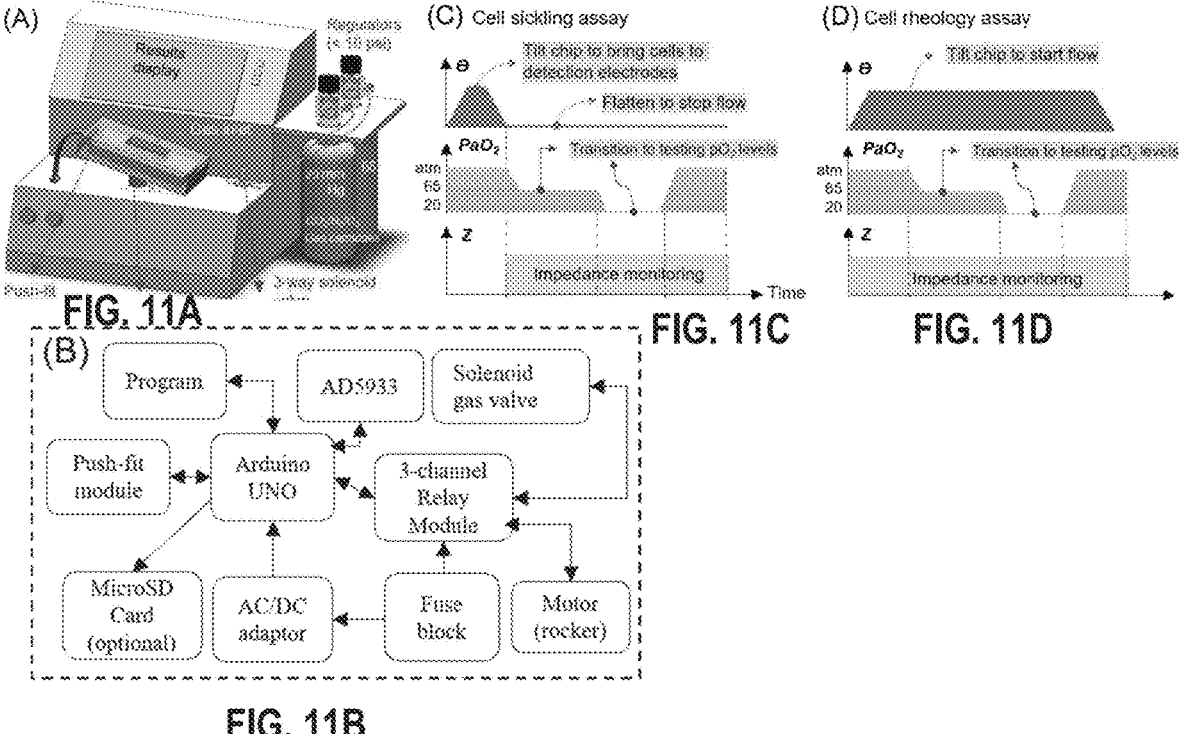

FIGS. 11A-11D are diagrams illustrating a pre-programmed instrument for automated blood-to results assays of $O_2$-dependent sickle cell functions. FIG. 11A shows a 3D model of an example instrument. FIG. 11B shows a diagram of the microcontroller-relay system with single push button to start. FIG. 11C and FIG. 11D depict an embedded program to streamline blood flow, $PaO_2$ control, and impedance Z monitoring for cell sickling assay and cell rheology assay, respectively.

Embodiments of the present disclosure provide a pre-programmed instrument for automated impedance measurement of $O_2$-dependent properties of sickle cells (FIG. 11A). The push-fit and rocker modules will be fully integrated into the standalone instrument. A schematic of the microcontroller-relay system is illustrated in FIG. 11B. It consists of a microcontroller (e.g., Arduino), a 3-channel relay module, AD5933 impedance converter chip, step motor (rocking), and 3-way pinch valve, and other necessary components packaged with a custom PCB inside an electromechanical case. The program can be developed in Arduino integrated development environment (IDE).

The 3-channel relay is pre-programmed to streamline the flow control by the rocker, $PaO_2$ control, and electrical impedance measurement according to the specific microfluidic assay (FIGS. 11C-11D), using the results from the optimization task described above. The operation variables, including angle $\theta$ and the triggering time points (t1-t3) will be pre-programmed to streamline the operation. In our current prototype, the portable impedance reading device is operated through a custom Android Application and data collected by a USB cable to a computer; impedance signals are analyzed by custom MATLAB scripts. These programs/codes can be optimized and compiled into a single program, towards a pre-programmed instrument to fully automate the measurements of sickling and rheological indices.

Performance of the μZAS system can be validated using spiked blood specimens as well as neat blood specimens drawn from SCD patients (n=30), recruited at the Alvarez's Sickle Cell Clinic with IRB approval. Results of the kinetics of cell sickling (sickling index, Š) and sickle cell rheology (rheological index, Ř), as quantified from the impedance signals will be validated with standard hematological assay. The ability of the μZAS in differentiation between normal blood, sickle cell trait (SCT) or simulant (~40% HbS), and homozygous SCD (HbSS), as well as between HbSS with and without HU treatment can be demonstrated.

Characterization of the analytical performance of the microfluidic assays. For validation, we can employ: (i) normal blood, (ii) normal blood spiked with sickle blood (with quantitative accuracy by mixing by volume fraction) at pathophysiologically relevant hematocrit values (e.g., 20-50%), and (iii) whole blood from diagnosed HbSS patients, including those treated with and without HU. The spiked specimens are useful to create a wide range of HbS levels, simulating different Hb genotypes and phenotypes (in case SCT not obtainable), as well as to simulate patients with RBC transfusion (in case not being obtainable).

Figure 12C:
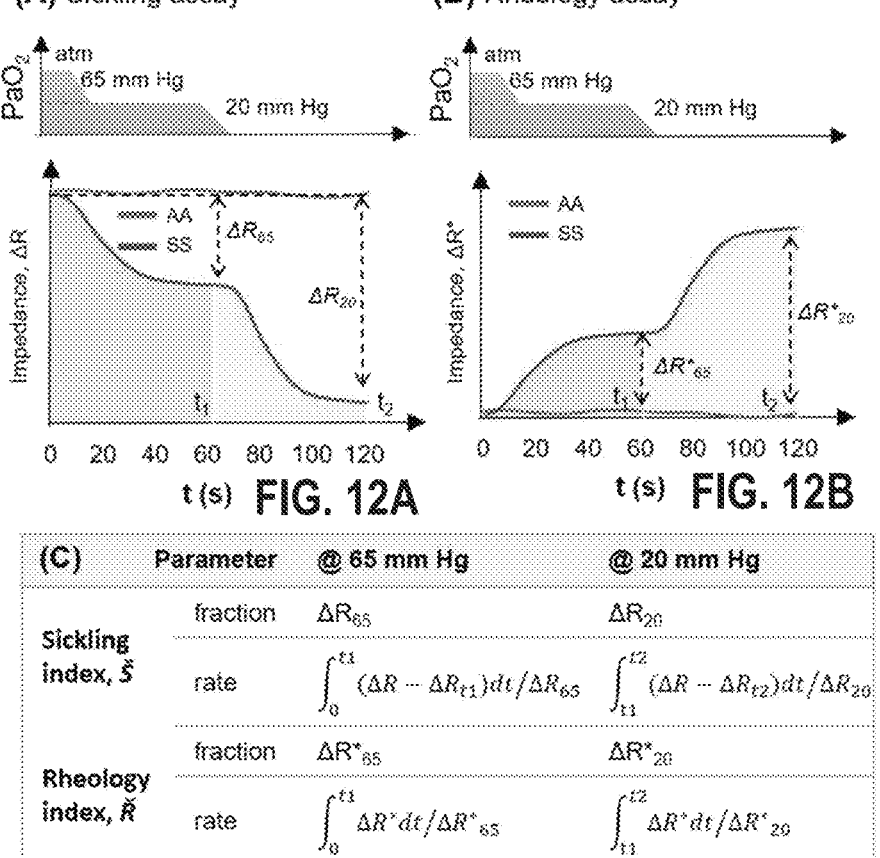
FIG. 12C demonstrates that Sickling index, Š and Cell rheology index, Ř can be derived and quantified from the impedance signals of sickle blood specimens in the corresponding microfluidic device.

Each microfluidic device can be pre-filled with buffers of known characteristics (e.g., phosphate-buffered saline, PBS). Whole blood specimens (1-10 μL) can be pipetted directly into the inlet of the cell channel of each microfluidic device. Parameters associated with cell sickling (i.e., sickled fraction & sickling rate) and blood rheology (i.e., occlusion fraction & occlusion rate) are quantified from impedance signals of sickle cell blood as illustrated in FIGS. 12A-12C which demonstrate quantification of $O_2$-dependent sickle cell functional properties from impedance signals. FIG. 12A illustrates sickling assay and FIG. 12B illustrates Rheology assay under a representative scenario when $PaO_2$ transitioned from atm to two testing values consecutively. AA and SS curves are exemplary. FIG. 12C demonstrates that Sickling index, Š and Cell rheology index, Ř can be derived and quantified from the impedance signals of sickle blood specimens in the corresponding microfluidic device (as shown, AA-normal blood, SS-sickle blood).

To evaluate the working range of microfluidic assays, a series of quality controls, such as LLOQ, LOW, MID, HIGH of hemolysate HbS level can be defined based on the Hb electrophoresis data. Limit of detection (LOD) can be identified per parameter/assay as well. Acceptance criteria of microfluidic assays for each biomarker parameter will be established. To confirm the fitness for purpose, we set the standard for the lower limit of quantification (LLOQ) extending beyond what may be required by −20% of 30% HbS level, which is selected by considering that clinical guidelines for red cell transfusion in severe SCD have a target endpoint, ~30% for HbS levels 103, 104, which is comparable to and even lower than the typical value (≤45%) found in asymptomatic sickle cell trait (SCT). We will report that the assays pass the sensitivity test if the LOD meets this criterion. The higher end of the range may subject to a small change depending on the availability of actual HbSS patient specimens, with HbS level confirmed by electrophoresis. Determinations will be obtained from at least three replicates of each 6 non-zero HbS % samples. Accuracy of the electrical impedance measurements will also be validated by microscopy-based analyses of cell morphological sickling and micro-slit obstruction.

The relationship between the impedance characterizations and the hematological measures, such as Complete Blood Count, Hb electrophoresis or HPLC, can be established as illustrated in FIGS. 5C-D, FIGS. 6A-C, and FIG. 7C. In the case when physicians do not order Hb electrophoresis for sickle blood specimens, Hb gel electrophoresis of hemolysate can be performed. Standard citrate agar electrophoresis and cellulose acetate electrophoresis can be performed to separate Hb variants, following standard procedure provided by manufacturers' instructions, against commercially available hemoglobin controls (Helena Laboratories), e.g., AFSA2 AFSC, and ASA2 standards.

It should be appreciated that the logical operations described herein with respect to the various figures may be implemented (1) as a sequence of computer-implemented acts or program modules (i.e., software) running on a computing device (e.g., the computing device described in FIG. 13), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special-purpose digital logic, and any combination thereof. It should also be appreciated that more or fewer operations may be performed than shown in the figures and described herein. These operations may also be performed in a different order than those described herein.

Figure 13:
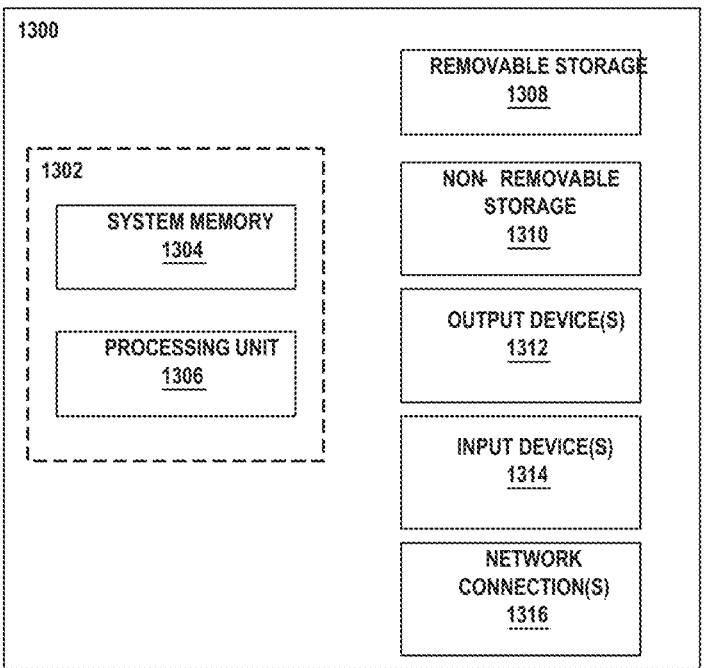
FIG. 13 is an example computing device.

Referring to FIG. 13, an example computing device 1300 upon which embodiments of the invention may be implemented is illustrated. This disclosure contemplates that the controller(s) for operating the flexure elements and/or imaging apparatus can be implemented using a computing device 1300. It should be understood that the example computing device 1300 is only one example of a suitable computing environment upon which embodiments of the invention may be implemented. Optionally, the computing device 1300 can be a well-known computing system including, but not limited to, personal computers, servers, handheld or laptop devices, multiprocessor systems, microprocessor-based systems, personal network computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In its most basic configuration, the computing device 1300 typically includes at least one processing unit 1306 and system memory 1304. Depending on the exact configuration and type of computing device, system memory 1304 may be volatile (such as random-access memory (RAM)), non-volatile (such as read-only memory (ROM), flash memory, etc.), or some combination of the two. This most basic configuration is illustrated in FIG. 13 by the dashed line 1302. The processing unit 1306 may be a standard programmable processor that performs arithmetic and logic operations necessary for the operation of the computing device 1300. The computing device 1300 may also include a bus or other communication mechanism for communicating information among various components of the computing device 1300.

Computing device 1300 may have additional features/functionality. For example, the computing device 1300 may include additional storage such as removable storage 1308 and non-removable storage 1310 including, but not limited to magnetic or optical disks or tapes. Computing device 1300 may also contain network connection(s) 1316 that allow the device to communicate with other devices. Computing device 1300 may also have input device(s) 1314 such as a keyboard, mouse, touch screen, etc. Output device(s) 1312, such as a display, speakers, printer, etc., may also be included. The additional devices may be connected to the bus in order to facilitate communication of data among the components of the computing device 1300. All these devices are well-known in the art and need not be discussed at length here.

The processing unit 1306 may be configured to execute program code encoded in tangible, computer-readable media. Tangible, computer-readable media refers to any media that is capable of providing data that causes the computing device 1300 (i.e., a machine) to operate in a particular fashion. Various computer-readable media may be utilized to provide instructions to the processing unit 1306 for execution. Example of tangible, computer-readable media may include but is not limited to, volatile media, non-volatile media, removable media and non-removable media implemented in any method or technology for storage of information such as computer-readable instructions, data structures, program modules or other data. System memory 1304, removable storage 1308, and non-removable storage 1310 are all examples of tangible computer storage media. Examples of tangible, computer-readable recording media include but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 1306 may execute program code stored in the system memory 1304. For example, the bus may carry data to the system memory 1304, from which the processing unit 1306 receives and executes instructions. The data received by the system memory 1304 may optionally be stored on the removable storage 1308 or the non-removable storage 1310 before or after execution by the processing unit 1306.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, for example, through the use of an application programming interface (API), reusable controls, or the like. Such programs may be implemented in a high-level procedural or object-oriented programming language to communicate with a computer system. However, the program(s) can be implemented in assembly or machine language if desired. In any case, the language may be a compiled or interpreted language, and it may be combined with hardware implementations.

Various illustrative logical blocks, modules, circuits, and algorithm operations described in connection with the embodiments disclosed herein may be implemented as electronic hardware, computer software, or combinations of both. To clearly illustrate this interchangeability of hardware and software, various illustrative components, blocks, modules, circuits, and operations have been described above generally in terms of their functionality. Whether such functionality is implemented as hardware or software depends upon the particular application and design constraints imposed on the overall system. Skilled artisans may implement the described functionality in varying ways for each particular application, but such embodiment decisions should not be interpreted as causing a departure from the scope of the claims.

The hardware used to implement various illustrative logics, logical blocks, modules, and circuits described in connection with the embodiments disclosed herein may be implemented or performed with a general-purpose processor, a digital signal processor (DSP), an application-specific integrated circuit (ASIC), a field programmable gate array (FPGA) or other programmable logic devices, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing systems (e.g., a combination of a DSP and a microprocessor, a plurality of microprocessors, one or more microprocessors in conjunction with a DSP core, or any other such configuration). Alternatively, some operations or methods may be performed by circuitry that is specific to a given function.

In one or more example embodiments, the functions described may be implemented in hardware, software, firmware, or any combination thereof. If implemented in software, the functions may be stored as one or more instructions or codes on a non-transitory computer-readable medium or non-transitory processor-readable medium. The operations of a method or algorithm disclosed herein may be embodied in a processor-executable software module, which may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc, where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

Those of skill in the art will appreciate that information and signals used to communicate the messages described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Whereas many alterations and modifications of the disclosure will no doubt become apparent to a person of ordinary skill in the art after having read the foregoing description, it is to be understood that any particular implementation shown and described by way of illustration is in no way intended to be considered limiting. Therefore, references to details of various implementations are not intended to limit the scope of the claims, which in themselves recite only those features regarded as the disclosure.

Definitions

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising," particularly in a description of components of a composition or in a description of elements of a device, can be exchanged with "consisting essentially of" or "consisting of." The invention illustratively described herein suitably may be practiced in the absence of any element or elements, limitation, or limitations which is not specifically disclosed herein. In each instance herein, any of the terms "comprising," "consisting essentially of," and "consisting of" may be replaced with either of the other two terms.

All patents and publications mentioned in the specification are indicative of the levels of skill of those skilled in the art to which the invention pertains. References cited herein are incorporated by reference herein in their entirety to indicate the state of the art as of their filing date, and it is intended that this information can be employed herein, if needed, to exclude specific embodiments that are in the prior art.

One skilled in the art will readily appreciate that the present invention is well adapted to carry out the objects and obtain the ends and advantages mentioned, as well as those inherent therein. The devices, device elements, methods, and materials described herein as presently representative of preferred embodiments are exemplary and are not intended as limitations on the scope of the invention. Changes therein and other uses will occur to those skilled in the art and are intended to be encompassed within this invention.

As used herein, "about" refers to a value that is 10% more or less than a stated value.

The patents, applications, and publications, as listed below and throughout this document, are hereby incorporated by reference in their entirety herein.

What is claimed is:

1. A micro-electrical impedance-based assay system (μZAS) for real-time monitoring of cellular response to an environmental condition, the μZAS comprising:
   at least one microfluidic device comprising:
      a cell channel configured to receive a sample substance;
      a gas channel network comprising a plurality of gas channels, the gas channel network being operatively coupled to the cell channel, wherein the gas channel network comprises at least one valve and at least one gas cartridge defining a controlled testing environment of the at least one microfluidic device; and
      a plurality of microfluidic impedance sensors configured to obtain, via one or more detection electrodes, electrical impedance-based measurement values with respect to the sample substance, wherein the at least one microfluidic device is operatively coupled to a gravity driven flow module configured to generate a gravity-driven hydrostatic pressure difference to drive a flow of the sample substance through the at least one microfluidic device; and
   a measurement instrument operatively coupled to the at least one microfluidic device that is configured to control a testing environment of the at least one microfluidic device.

2. The μZAS of claim 1, further comprising:
   a controller operatively coupled to the measurement instrument that is configured to determine and output at least one measurement value in relation to the sample substance to provide quantitative assessment of a hematological condition or outcome.

3. The μZAS of claim 2, wherein the controller is configured to determine at least one of a sickling index and/or sickle cell rheology.

4. The μZAS of claim 2, wherein the controller is configured to detect a change in electrical impedance above a predetermined threshold that is indicative of an abnormal blood flow.

5. The μZAS of claim 2, wherein the controller is configured to detect a $PaO_2$ transition resulting from resistance to electric currents associated with a corresponding sickling event.

6. The μZAS of claim 2, further comprising:
   a display device or monitor operatively coupled to the μZAS and the controller configured to output at least a portion of the electrical impedance-based measurement values.

7. The μZAS of claim 1, wherein at least one of the electrical impedance-based measurement values is used to evaluate treatment efficacy for sickle cell disease, determine a biophysical marker of diabetes, assess whether blood flow is normal under hypoxia, or to evaluate dosage-dependencies of blood flow on medications.

8. The μZAS of claim 1, wherein the measurement instrument is configured to measure a rate of blood flow through the at least one microfluidic device.

9. The μZAS of claim 1, wherein the at least one microfluidic device and the measurement instrument are operatively coupled to one another via a magnetic, force, or snap-fit connection.

10. The μZAS of claim 1, wherein the at least one microfluidic device further comprises at least one microstructure for measuring a flow condition or obstruction.

11. The μZAS of claim 1, wherein each the at least one-gas channel is configured to supply at least a first gaseous substance and a second gaseous substance.

12. The μZAS of claim 1, wherein the gas channel network comprises a single inlet and a single outlet.

13. The μZAS of claim 1, wherein the plurality of microfluidic impedance sensors is positioned within the gas channel network.

14. The μZAS of claim 1, wherein the gravity driven flow module comprises a rocker module configured to facilitate programmable gravity-driven flow.

15. The μZAS of claim 1, wherein the μZAS is configured for blood testing under a plurality of controlled $O_2$ conditions or $PaO_2$ conditions.

16. The μZAS of claim 1, wherein the at least one microfluidic device comprises at least one disposable chip.

17. The μZAS of claim 1, wherein the plurality of microfluidic impedance sensors comprises 16 microfluidic impedance sensors.

18. A micro-electrical impedance-based assay system (μZAS) for real-time monitoring of cellular response to an environmental condition comprising a plurality of microfluidic devices, each microfluidic device comprising:
   a cell channel configured to receive a sample substance;
   a gas channel network comprising a plurality of gas channels, the gas channel network being operatively coupled to the cell channel, wherein the gas channel network comprises at least one valve and at least one gas cartridge defining a controlled testing environment of each of the plurality of microfluidic devices; and
   a plurality of microfluidic impedance sensors configured to obtain electrical impedance-based measurements with respect to the sample substance, wherein:
   each microfluidic device is operatively coupled to a gravity driven flow module configured to generate a gravity-driven hydrostatic pressure difference to drive a flow of the sample substance through each respective microfluidic device, and
   the plurality of microfluidic devices is operatively coupled to a measurement instrument that is configured to control a testing environment of each microfluidic device.

* * * * *